United States Patent
Kimura et al.

(10) Patent No.: US 7,822,558 B2
(45) Date of Patent: Oct. 26, 2010

(54) FLUORESCENCE DETECTING DEVICE AND FLUORESCENCE DETECTING METHOD

(75) Inventors: Noriaki Kimura, Osaka (JP); Kyoji Doi, Okayama (JP); Takayoshi Yumii, Okayama (JP); Takashi Yoshida, Osaka (JP); Shigeyuki Nakada, Okayama (JP); Hironori Hayashi, Okayama (JP); Kazuteru Hoshishima, Okayama (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 472 days.

(21) Appl. No.: 11/816,244

(22) PCT Filed: Feb. 15, 2006

(86) PCT No.: PCT/JP2006/302633
§ 371 (c)(1),
(2), (4) Date: Aug. 14, 2007

(87) PCT Pub. No.: WO2006/088047
PCT Pub. Date: Aug. 24, 2006

(65) Prior Publication Data
US 2009/0012721 A1 Jan. 8, 2009

(30) Foreign Application Priority Data
Feb. 15, 2005 (JP) ............................ 2005-037399
Sep. 29, 2005 (JP) ............................ 2005-285084

(51) Int. Cl.
*G06F 19/00* (2006.01)
(52) U.S. Cl. ........................................ 702/23; 356/32
(58) Field of Classification Search ................ 702/23, 702/182–185; 356/32, 35.5, 36, 300, 303, 356/451
See application file for complete search history.

(56) References Cited

U.S. PATENT DOCUMENTS 5,270,548 A 12/1993 Steinkamp ............... 250/461.2

(Continued)

FOREIGN PATENT DOCUMENTS

JP 2-262038 10/1990

(Continued)

OTHER PUBLICATIONS

Non-patent document cited in the application: www://bdbiosciences.com/pharmingen/protocols/Fluorochrome_Absorption.shtml; Fluorochrome Absorption and Emission Spectra, pp. 1 to 7.

(Continued)

*Primary Examiner*—Edward Raymond
(74) *Attorney, Agent, or Firm*—Whitham Curtis Christofferson & Cook, PC

(57) ABSTRACT

A fluorescence detecting device irradiates an object to be measured with a laser beam, receives fluorescence generated from the object and processes a fluorescence signal generated when receiving the fluorescence. The device includes a laser light source section outputting the laser beam for irradiating the object, a light receiving section outputting the fluorescence signal of the fluorescence generated by the irradiated object, a light source control section generates a modulation signal having a frequency in order to time-modulate an intensity of the laser beam, and a processing section that calculates a fluorescence relaxation time of the fluorescence of the object based on the fluorescence signal output from the light receiving section. From the detection values acquired by the device including the phase information on the fluorescence, the intensity of the fluorescence is calculated.

19 Claims, 12 Drawing Sheets

U.S. PATENT DOCUMENTS

| | | | |
|---|---|---|---|
| 5,315,122 A | 5/1994 | Pinsky et al. | 250/461.2 |
| 5,317,162 A | 5/1994 | Pinsky et al. | 250/461.2 |
| 5,504,337 A | 4/1996 | Lakowicz et al. | 250/461.2 |
| 6,592,822 B1 | 7/2003 | Chandler | |
| 2004/1199974 | 6/2004 | Bishop | |

FOREIGN PATENT DOCUMENTS

| | | |
|---|---|---|
| JP | 8-086753 | 4/1996 |
| JP | 8-506419 T | 7/1996 |
| JP | 9-329548 | 12/1997 |
| JP | 2003-083894 | 3/2003 |
| JP | 2004-020262 | 1/2004 |

OTHER PUBLICATIONS

Keji, J., et al., "Flow Cytometric Characterization and Classification of Multiple Dual-Color Fluorescent Micropsheres Using Fluorescence Lifetime", Cytometry, Jan. 1, 1998., vol. 33, No. 3. pp. 318-323.

European Search Report dated May 11, 2010.

FLUORESCENCE DETECTING DEVICE AND FLUORESCENCE DETECTING METHOD

TECHNICAL FIELD

The present invention relates to a fluorescence detecting device and a fluorescence detecting method, in which an object to be measured is irradiated with a laser beam that has been subjected to intensity modulation, a fluorescence signal from the object to be measured which is attributable to the irradiation is received, and signal processing is conducted on the signal. The fluorescence detecting device and the fluorescence detecting method are applied to, for example, an analyzing device, such as a flow cytometer used in a medical or biological field, which is capable of analyzing the object to be measured in a short period of time by identifying fluorescence that is emitted by a fluorochrome due to irradiation of the laser beam to thereby identify the object to be measured while the object to be measured is flowing in a sheath solution. More particularly, the present invention relates to a fluorescence detecting device and a fluorescence detecting method, in which respective fluorescence intensities are obtained by using fluorescence detected values of plural labeled samples, the fluorescence detected values being generated by irradiating the plural labeled samples with the laser beam at the same time by using the flow cytometer or the like.

BACKGROUND ART

A fluorescence detecting device that receives fluorescence from the fluorochrome of the object to be measured by irradiating the object to be measured with the laser beam to identify the type of the object to be measured is employed in the flow cytometer used in the medical or biological field.

Specifically, the flow cytometer is a device that mixes samples such as cells, DNAs, RNAs, enzymes, proteins, or micro beads, which are labeled as the fluorochrome, with a normal saline to produce a sample solution by using the binding of antigen-antibody reaction and the like. Then, the device allows the sample solution to flow so as to be encompassed with another solution called "sheath solution", resulting that a laminar sheath flow in which the labeled samples flow at a speed of about 10 m or lower per second is formed while a pressure is exerted on the laminar sheath flow. The device irradiates the sheath flow with a laser beam to measure the fluorescence or a scattered light in each of the samples. For example, in the case where a variety of samples are to be analyzed, the flow cytometer measures the fluorescent intensity of the fluorescence that is generated by the sample, and identifies which sample having which fluorescence characteristics has passed by among the many kinds of samples. In this case, labeled samples to which fluorochromes of different kinds are adhered are used for the many kinds of samples. The flow cytometer irradiates the labeled sample with the laser beam, and measures the fluorescence that is generated with the irradiation of the laser beam.

Further, the flow cytometer is capable of measuring an intracellular relative quantity of, for example, DNAs, RNAs, enzymes, or proteins within a cell, and also analyzing activity thereof in a short time. Further, there is used a cell sorter that specifies a specific type of cell or chromosome by fluorescence, and selectively collects only the specific cell or chromosome in a live state in a short time.

In the use of the cell sorter, it is required to specify more objects to be measured from information on fluorescence in a short time.

In the following Non-patent Document 1, there is disclosed a flow cytometer that irradiates fluorochromes with plural laser beams that are different in the wavelength band such as 488 nm, 595 nm, and 633 nm, separates plural kinds of fluorescence that are different in the wavelength band which are generated from the fluorochrome by the respective laser beams by using a band pass filter, and detects the separated fluorescence by means of a photoelectron multiple tube (PMT). With the above configuration, it is possible to identify the fluorescence from the plural fluorescent reagents (fluorochrome) to specify the plural kinds of objects to be measured at once.

However, although the wavelength range of the fluorescence that is generated from the fluorescent reagent has a relatively wide width such as about 400 to 800 nm, only 3 to 4 wavelength bands of the fluorescent reagent can be effectively used for an identifiable labels in the visible wavelength range. An increase in the number of fluorescence that can be identified by employing the plural fluorescent reagents is restricted.

Further, in order to increase the number of identifiable fluorescence, it is possible to increase the number of identifiable fluorescence by using the wavelength of fluorescence as well as the intensity of detected fluorescence. However, even in this case, the number of identifiable fluorescence by using the intensity of fluorescence is about 2 to 5, and even if this number is combined with the above-mentioned number of identifiable fluorescence of about 3 to 4 wavelength bands, the number of identifiable fluorescence is about 20 at maximum. For that reason, there arises such a problem that it is difficult to identify and analyze an extremely large number of objects to be measured in a short time even if the above flow cytometer is used.

For example, in the case where a biologic material such as DNA is analyzed by the flow cytometer, fluorochrome is adhered to the biologic material with a fluorescent reagent in advance, and the biologic material is labeled by a fluorochrome different from fluorochromes that have been adhered to micro beads which will be described later. Then, the biologic material is mixed with a solution containing micro beads of 5 to 20 μm in diameter, the micro beads having a surface provided with a unique structure such as carboxyl group. The structure of carboxyl group acts on a biologic material of a certain known structure, and conducts a biological coupling therewith. Accordingly, in the case where the flow cytometer detects fluorescence from the micro beads and fluorescence of the biologic material at the same time, it is found that the biologic material is biologically coupled with the structure of the micro beads. As a result, it is possible to analyze the characteristic of the biologic material. However, in order to analyze the characteristics of the biologic material in a short time by providing various micro beads having various coupling structures, an extremely large number of kinds of fluorochromes are required. However, since the number of kinds of fluorescent reagents identifiable at the same time is small, it is impossible to analyze the biologic material efficiently in a short time by using a large variety of micro beads at once.

Further, there is proposed a method in which plural measurement points at which an object to be measure is irradiated with laser beams to measure fluorescence are provided in the longitudinal direction of a flow tube, and the laser beams irradiated at the respective measurement points are prevented from interfering with each other. However, in this case, it is necessary to provide a large number of laser beams and a large number of light receiving sections in correspondence with the number of measurement points. Further, since a flow tube that forms the flow cell is elongated, the flow path resistance of the sheath solution that flows in the tube becomes large, and a pressure to be exerted on the sheath solution becomes large. For that reason, there arises such a problem that the device is increased in size.

Further, when fluorescence is measured by using the flow cytometer, it is necessary to measure and identify the fluorescence generated by a large variety of fluorochromes and the autofluorescence generated by the samples per se such as the cells or the micro beads at the same time. For that reason, the flow cytometer is equipped with plural photoelectric converters that are different in received light wavelength band from each other, and the fluorochromes that match the received light wavelength bands are selected and used, respectively. In this situation, the measured values that have been obtained by the plural photoelectric converters represent the fluorescence intensities in the respective fluorochromes. However, when the plural kinds of fluorescence are received in the received light wavelength range of the photoelectric converters at the same time, the measured results of the fluorescence intensities are deviated from the actual fluorescence intensities. In order to correct this deviation, the detected values are generally corrected.

As the above correction, for example, there is disclosed a fluorescence value correcting method in the following Patent Document 1.

According to the following Patent Document 1, the measured values that have been obtained by the plural photoelectric converters are represented as vectors. On the other hand, the inverse matrix of a predetermined correction matrix is produced, and the produced inverse matrix acts on the above vectors, thereby enabling the real fluorescence intensities to be calculated. In this case, as shown in FIGS. 8B and 9B of Patent Document 1, the correction matrix is a matrix of geometric transformation which corrects the positional relationship in a two-dimensional correlation diagram (scattergram). For that reason, in order to produce the inverse matrix from the correction matrix and make the inverse matrix act on the vectors having the measured values as vector elements, it is required that the correction matrix is a square matrix. The matrix size of the correction matrix is determined according to the number of photoelectric converters that output the measured values, and a sum of the number of kinds of the autofluorescence generated by the samples (objects to be measured) such as the micro beads or the cells and the number of kinds of the fluorescence generated by the fluorochromes adhered to the samples. As a result, in order for the correction matrix to be the square matrix, the number of photoelectric converters must be made equal to the number of received fluorescence. In other words, when there are provided four kinds of fluorochromes that are adhered to the samples such as the micro beads or the cells, the measurement needs to be conducted by a total of those four fluorochromes and one kind of autofluorescence, that is, five photoelectric converters. The measurement using a large number of photoelectric converters causes an increase in the number of arranged photoelectric converters as well as an increase in the number of processor circuits that process the measured values. As a result, the costs of the flow cytometer and the processing devices are increased. For that reason, there arises such a problem that the kinds of identifiable fluorescence that are measured at the same time are restricted in the number according to the number of arranged photoelectric converters.

Non-patent Document 1: http://www.bdbiosciences.com/pharmingen/protocols/Fluorochrome_Absorption.shtml (searched on Jan. 23, 2005)

Patent Document 1: JP-A-2003-83894

DISCLOSURE OF THE INVENTION

Problems to be solved by the Invention

Under the circumstances, to solve the above problems, it is an object of the present invention to provide a fluorescence detecting device which is capable of identifying the kinds of fluorescence that is generated from a large number of samples that are objects to be measured such as micro beads through signal processing. In particular, the device is capable of identifying fluorescence signals efficiently in a short time, when the fluorescence detecting device irradiates the objects to be measured with a laser beam and receives fluorescence signals from the objects to be measured to conduct signal processing. For example, the fluorescence detecting device is preferably used in a flow cytometer. Another object of the present invention is to provide a fluorescence detecting method, a fluorescence detecting device, and a fluorescence detecting method, which are capable of increasing the number of kinds of identifiable fluorochromes that are measured at the same time as compared with the conventional art in the case of obtaining the respective fluorescence intensities by using the detected values of fluorescence generated by irradiating, with the laser beam, labeled samples that are labeled with plural fluorochromes.

Means for Solving the Problems

The present invention provides a fluorescence detecting device using an intensity-modulated laser beam, which irradiates an object to be measured with a laser beam to receive fluorescence generated by the object to be measured, and carries out signal processing of a fluorescence signal obtained when receiving the fluorescence, comprising: a laser light source section that outputs the laser beam with which the object to be measured is irradiated; a light receiving section that outputs the fluorescence signal of the fluorescence generated by the object to be measured which is irradiated with the laser beam; a light source control section that generates a modulation signal having a given frequency in order to time-modulate an intensity of the laser beam that is output from the laser light source section; and a processing section that calculates, by using the modulation signal, a fluorescence relaxation time of the fluorescence of the object to be measured based on the fluorescence signal that is output from the light receiving section by irradiating the object to be measured with the time-modulated laser beam.

In the invention, the processing section preferably obtains a phase delay with respect to the modulation signal of the fluorescence signal to calculate the fluorescence relaxation time.

Preferably, the light source control section uses as a pulse control signal a coding sequence signal that is selected from a plurality of coding sequence signals which have signal values of one bit coded with a given length and are orthogonal to each other, and sets and controls on/off of output of the laser beam so that an on-time of the output of the laser beam from the laser light source section is longer than one cycle time of the time modulation of the laser beam, and the processing section calculates the fluorescence relaxation time and identifies the fluorescence from the object to be measured, by using the coding sequence signal based on a light receiving signal that is output from the light receiving section. Here, the plurality of coding sequence signals are preferably configured by shifting one coding sequence signal in a bit direction and the coding sequence signals become orthogonal to each other by the shifting.

Preferably, the laser light source section includes a plurality of laser light sources that output a plurality of laser beams, wherein the light source control section controls the on/off of outputs of the laser beams from the plurality of laser light sources by using the plurality of coding sequence signals that are orthogonal to each other, and wherein the processing section separates each of fluorescence signals of the fluorescence that is generated by the object to be measured by irradiation of the respective laser beams, from the fluorescence signals which are overlapped together and outputted from the light receiving section, including optical signals of the plurality of laser beams, by using the coding sequence signals used for the outputs of the laser beams.

Preferably, the object to be measured includes a plurality of labeled samples that are labeled by a plurality of fluorochromes that generate different kinds of fluorescence, wherein the light receiving section includes an input section that acquires, by receiving fluorescence of the labeled samples generated by irradiation of the laser beam by a plurality of detection sensors that are different in light receiving wavelength band, detected values of the fluorescence signal including phase information from each of the respective detection sensors, and wherein the processing section includes:

a matrix producing section that calculates fluorescence relaxation times of the fluorescence that is generated by the fluorochromes, and sets matrix elements of a correction conversion matrix for obtaining fluorescence intensities by using the calculated fluorescence relaxation times, to thereby produce the correction conversion matrix; and an intensity calculating section that obtains, with a set of the detected values of the fluorescence signals including the phase information acquired from the respective detection sensors as a vector, the fluorescence intensities of the fluorescence that is generated by the respective labeled samples by allowing an inverse matrix produced from the correction conversion matrix to act on the vector.

Preferably, the labeled samples include a plurality of different kinds of samples by adhering the fluorochromes that are different in kind from each other to samples that generate autofluorescence by irradiation of the laser beam, and wherein the fluorescence that is generated from at least one kind of fluorochrome among the fluorochromes and the autofluorescence that is generated from the samples by irradiation of the labeled samples with the laser beam have wavelength spectrums partially overlapped each other in a wavelength region. The processing section preferably includes a first calibration section that obtains the fluorescence relaxation time and a gain constant when it is assumed that the autofluorescence is a relaxation response of a first order lag system in an unlabeled sample, where a sample to which any fluorochrome are not adhered and which generates the autofluorescence is referred to as the unlabeled sample, wherein the first calibration section acquires the detected values including the phase information from the respective detection sensors when the unlabeled sample is irradiated as the object to be measured with the laser beam that has been modulated in time at the given frequency, and obtains the fluorescence relaxation time and the gain constant of the autofluorescence that is generated by the unlabeled sample based on the detected values, and wherein the matrix producing section produces the correction conversion matrix by using the fluorescence relaxation time and the gain constant obtained by the first calibration section.

The processing section preferably includes a second calibration section that obtains, for each kind of the labeled samples, the fluorescence relaxation time and the gain constant when it is assumed that the fluorescence that is generated by each fluorochrome is a relaxation response of a first order lag system for each kind of the labeled samples, wherein the second calibration section acquires the detected values including the phase information from the respective detection sensors when a labeled sample, in which one kind of the fluorochromes is adhered to a sample that generates the autofluorescence is irradiated as the object to be measured with the laser beam that has been modulated in time at the given frequency, obtains the fluorescence relaxation time and a gain constant of the fluorescence that is generated by the fluorochrome of the labeled sample based on the detected values, and obtains fluorescence relaxation times and gain constants of the fluorescence that is generated by all of the fluorochromes included in the labeled samples while changing the kind of the fluorochrome that is adhered to the sample that generates the autofluorescence, and wherein the matrix producing section produces the correction conversion matrix by using the fluorescence relaxation times and the gain constants of the labeled samples obtained by the second calibration section.

The invention further provides a fluorescence detecting device that irradiates a plurality of labeled samples that are labeled by a plurality of fluorochromes with a laser beam to obtain respective fluorescence intensities based on detected values of fluorescence of the plurality of labeled samples that generate different kinds of fluorescence, comprising: a laser light source section that outputs the laser beam with which the object to be measured is irradiated; a light receiving section that outputs a fluorescence signal of the fluorescence that is generated from the object to be measured which is irradiated with the laser beam; a light source control section that generates a modulation signal having a given frequency in order to time-modulate an intensity of the laser beam that is output from the laser light source section; and a processing section that calculates a fluorescence relaxation time of the fluorescence of the object to be measured by using the modulation signal based on the fluorescence signal that is output from the light receiving section by irradiating the object to be measured with the time-modulated laser beam, wherein the light receiving section includes a plurality of detection sensors that are different in light receiving wavelength band, for receiving the fluorescence of the labeled samples when the intensity of the laser beam is modulated in time at a given frequency and the labeled samples are irradiated with the laser beam, and wherein the processing section includes:

an input section that acquires, by receiving the fluorescence of the labeled samples by the plurality of detection sensors, the detected values including phase information from the respective detection sensors;

a matrix producing section that sets matrix elements of a correction conversion matrix to produce the correction conversion matrix by using parameters of a transfer function when it is assumed that each fluorescence of the labeled samples that are irradiated with the laser beam is a relaxation response of a first order lag system; and an intensity calculating section that obtains, with a set of the detected values including the phase information acquired from the respective detection sensors as a vector, the fluorescence intensities of the fluorescence that is generated by the respective labeled samples by allowing an inverse matrix produced from the correction conversion matrix to act on the vector.

The invention also provides a fluorescence detecting method, which is a fluorescence intensity calculating method of obtaining respective fluorescence intensities based on detected values of fluorescence that is generated by irradiating a plurality of labeled samples with a laser beam, the labeled samples being labeled by a plurality of fluorochromes, the fluorescence detecting method comprising the steps of: time-modulating an intensity of the laser beam in time at a given frequency, irradiating the labeled samples with the time-modulated laser beam, and receiving the fluorescence generated by the labeled samples at this time by a plurality of detection sensors that are different in light receiving wavelength band, to thereby acquire the detected values including phase information from the respective detection sensors; producing the correction conversion matrix by setting matrix elements of the correction conversion matrix using parameters of a transfer function when it is assumed that each fluorescence of the labeled samples that are irradiated with the laser beam is a relaxation response of a first order lag system; and obtaining, with a set of the detected values including the phase information acquired from the respective detection sensors as a vector, the fluorescence intensities of the fluorescence that is generated by the labeled samples by allowing an inverse matrix produced from the correction conversion matrix to act on the vector.

In the invention, the labeled samples preferably includes a plurality different kinds of samples by adhering the fluorochromes that are different in kind from each other to samples that generate autofluorescence with irradiation of the laser beam, and wherein the fluorescence that is generated from at least one kind of fluorochrome among the fluorochromes and the autofluorescence that is generated from the samples have wavelength spectrums partially overlapped each other in a wavelength region by irradiation of the labeled samples with the laser beam.

In the fluorescence detecting method, when the number of the detection sensors is m and the number of kinds of the fluorochromes is n, $2 \cdot m \geq n+1$ is satisfied.

Preferably, the step of producing the correction conversion matrix includes performing a first calibration for obtaining, where a sample to which the fluorochrome is not adhered and which generates the autofluorescence is referred to as an unlabeled sample, a fluorescence relaxation time and a gain constant when it is assumed that the autofluorescence is a relaxation response of a first order lag system for the unlabeled sample, wherein the first calibration includes irradiating the unlabeled sample as an object to be measured with the laser beam that has been modulated in time at the given frequency to acquire the detected values including the phase information from the respective detection sensors, and obtaining a fluorescence relaxation time and a gain constant of the autofluorescence that is generated by the unlabeled sample based on the detected values, and wherein the correction conversion matrix is produced by using the fluorescence relaxation time and the gain constant obtained by the first calibration. In the producing of the correction conversion matrix, when the gain constant that is obtained by the first calibration is used in order to produce the correction conversion matrix, gain constants that are obtained from the detected values of the respective detection sensors are preferably used after normalizing the gain constants by a maximum gain constant among the gain constants. Preferably, in the first calibration, the detected values used for obtaining the fluorescence relaxation time and the gain constant comprise amplitude values of a cos component and a sin component of a signal waveform detected by the detection sensors, the detected values including the phase information are acquired for each of the labeled samples, and a representative value is extracted from the plurality of detected values to be used in the first calibration.

Preferably, the step of producing the correction conversion matrix includes performing a second calibration for obtaining, for each kind of the labeled samples, the fluorescence relaxation time and the gain constant when it is assumed that the fluorescence that is generated by the fluorochrome is a relaxation response of a first order lag system, for each kind of the labeled samples, wherein the second calibration includes irradiating a labeled sample, in which one kind of the fluorochromes is adhered to a sample that generates the autofluorescence, as the object to be measured with the laser beam that has been modulated in time at the given frequency to acquire the detected values including the phase information from the respective detection sensors, obtaining the fluorescence relaxation time and the gain constant of the fluorescence that is generated by the fluorochrome of the labeled sample based on the detected values, and obtaining fluorescence relaxation times and gain constants of the fluorescence that is generated by all of the fluorochromes included in the labeled samples while changing the kind of the fluorochrome that is adhered to the sample that generates the autofluorescence, and wherein the correction conversion matrix is produced by using the fluorescence relaxation times and the gain constants which are obtained by the second calibration.

In the obtaining of the fluorescence relaxation times and the gain constants of the fluorescence that is generated by the fluorochromes of the labeled samples, when a sample to which the fluorochrome is not adhered and which generates the autofluorescence is referred to as an unlabeled sample, the first calibration for obtaining the fluorescence relaxation time and the gain constant is preferably performed for the unlabeled sample, the fluorescence relaxation time and the gain constant defined when it is assumed that the autofluorescence is a relaxation response of the first order lag system is performed for the unlabeled sample, and wherein the second calibration includes obtaining the fluorescence relaxation times and the gain constants of the fluorescence that is generated by the fluorochromes of the labeled samples by using the fluorescence relaxation time and the gain constant of the fluorescence that is generated by the unlabeled sample, the fluorescence relaxation time and the gain constant of the fluorescence that is generated by the unlabeled sample being obtained based on the detected values including the phase information acquired from the respective detection sensors by irradiating the unlabeled sample as the object to be measured with the laser beam that has been modulated in time at the given frequency in the first calibration. Preferably, in the producing of the correction conversion matrix, when the gain constants obtained by the second calibration are used in order to produce the correction conversion matrix, the gain constants that are obtained from the detected values of the respective detection sensors are normalized by a maximum gain constant among the gain constants of the fluorescence that is generated by the fluorochromes of the respective labeled samples.

In the second calibration, the detected values used for obtaining the fluorescence relaxation times and the gain preferably constants comprise amplitude values of a cos component and a sin component of a signal waveform detected by the detection sensors, the detected values including the phase information are acquired for respective labeled samples, and a representative value is extracted from the detected values of the plurality of labeled samples to be used in the second calibration.

EFFECTS OF THE INVENTION

According to the present invention, micro beads etc. are set as objects to be measured, and the objects to be measured are irradiated with a laser beam that has been modulated in intensity at a given frequency to obtain a fluorescence relaxation time of the fluorescence that is generated by the irradiation with the laser beam. Since the fluorescence relaxation time varies depending on the kind of fluorochromes, it is possible to identify the kinds of fluorescence, particularly the kinds of objects to be measured by using the fluorescence relaxation time. In other words, since the fluorescence relaxation time can be used to identify the fluorescence besides the wavelength of fluorescence and the intensity of fluorescence which have been conventionally used to identify the fluorescence, the number of identifiable kinds of fluorescence is increased. In particular, the present invention is effective for a flow cytometer that efficiently specifies the object to be measured in a short time by using a large number of fluorochromes.

Further, in the case of using plural laser beams, coding sequence signals that are orthogonal to each other in each of the laser beams are used as pulse control signals of the laser beams, thereby making it possible to specify which laser beam causes the received fluorescence signal to be generated by the irradiation. As a result, it is possible to efficiently specify the objects to be measured in a short time.

Further, according to the present invention, even if the labeled samples that are labeled with the plural fluorochromes are irradiated with the laser beams, it is possible to obtain gain constants corresponding to the fluorescence intensities. In this situation, since the laser beams are modulated in time at a given frequency, it is possible to detect phase difference information from one photoelectric converter. Accordingly, since the fluorescence intensities are obtained by using those values, the number of kinds of identifiable fluorescence from the measurement can be increased as compared with the conventional art when the number of arranged photoelectric converter is fixed.

Further, since a first calibration and a second calibration for calculating fluorescence relaxation time constants and gain constants by using an unlabeled sample and the respective labeled samples are conducted before the fluorescence intensities of the plural kinds of labeled samples are calculated, it is possible to obtain the fluorescence intensities of the plural kinds of labeled samples with high precision.

Figure 1:
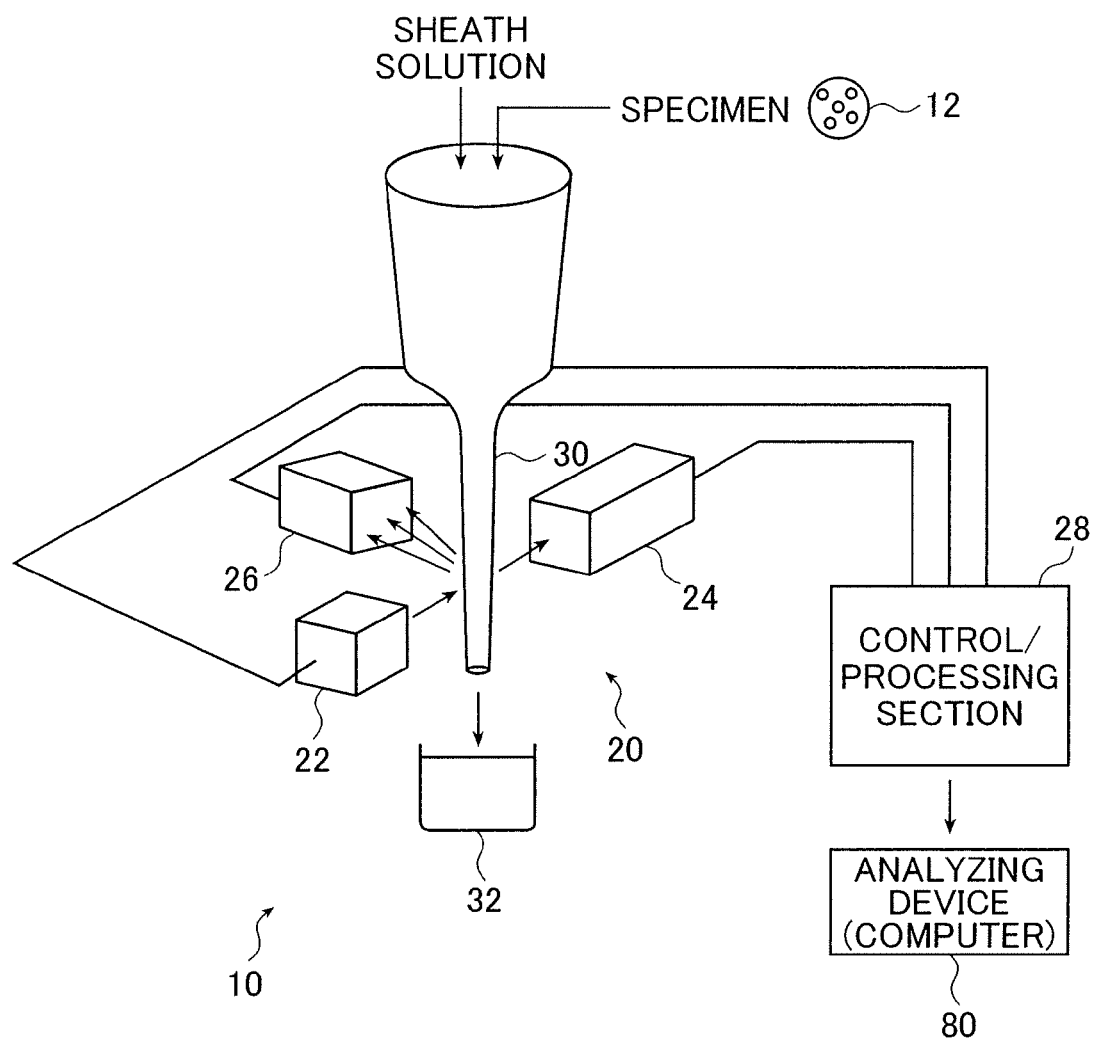
FIG. 1 is a schematic structural diagram showing a flow cytometer using a fluorescence detecting device that uses an intensity-modulated laser beam according to the present invention.

DESCRIPTION OF SYMBOLS 10, 110 flow cytometer
12 specimen
20, 120 signal processing device
22, 122 laser light source section
22$r$ R light source
22$g$ G light source
22$b$ B light source
23$a_1$, 23$a_2$, 26$b_1$, 26$b_2$ dichroic mirror
23$c$, 26$a$, 126$a$ lens system
24, 26, 124, 126 light receiving section
26$c_1$, 26$c_2$, 26$c_3$, 126$c_1$, 126$c_2$, 126$c_3$ band pass filter
27$a$-27$c$, 127$a$-127$c$ photoelectric converter
28, 128 control/processing section
30, 130 tube
32, 132 collecting vessel
34$r$, 34$g$, 34$b$ laser driver
35, 48, 56 power splitter
40, 140 signal generating section
42, 142 signal processing section
44, 144 controller
46, 146 oscillator
50, 52, 54$a$, 54$b$, 54$c$, 64, 150, 152, 154$a$, 154$b$, 154$c$, 164 amplifier
58$a$, 58$b$, 58$c$ IQ mixer
60, 160 system controller
62, 162 low pass filter
66, 166 A/D converter
80, 180 analyzing device
112 labeled sample
156 phase difference detector
182 CPU
184 memory 186 input/output port
188 first calibration unit
190 second calibration unit
192 intensity calculating unit

BEST MODE FOR CARRYING OUT THE INVENTION

Hereinafter, a description will be given in more detail of a flow cytometer that preferably uses a fluorescence detecting device and a fluorescence detecting method using an intensity-modulated laser beam according to the present invention.

First, a first embodiment of the present invention will be described.

FIG. 1 is a schematic structural diagram showing a flow cytometer 10 using a fluorescence detecting device using an intensity-modulated laser beam according to the present invention.

A flow cytometer 10 includes a signal processing device 20 that irradiates a specimen 12 such as micro beads to be measured with a laser beam, and detects a fluorescence signal of fluorescence that is generated by fluorochromes disposed in the specimen 12 to process a signal, and an analyzing device (computer) 80 that analyzes the objects to be measured in the specimen 12 on the basis of the processed results that have been obtained by the signal processing device 20.

The signal processing device 20 includes a laser light source section 22, light receiving sections 24 and 26, a control/processing section 28 including a control section that modulates in intensity the laser beam from the laser light source section 22 at a given frequency and controls the on/off operation of output of the laser beam, and a signal processing section that identifies a fluorescence signal from the specimen 12, and a tube 30 that allows the specimen 12 included in a sheath solution which forms a high speed flow, thereby forming a flow cell.

A collecting vessel 32 is disposed at the outlet of the tube 30. A cell sorter for separating biologic material such as specific cells in the specimen 12 within a short time after the irradiation of the laser beam may be disposed in the flow cytometer 10 so as to separate the biologic material in different collecting vessels.

The laser light source section 22 is a section that outputs three laser beams different in wavelength, for example, laser beams of $\lambda_1=405$ nm, $\lambda_2=533$ nm, and $\lambda_3=650$ nm. A lens system is disposed in such a manner that the laser beam is focused to a given position within the tube 30. A measurement point of the specimen 12 is defined at the focus position of the laser beam.

Figure 2:
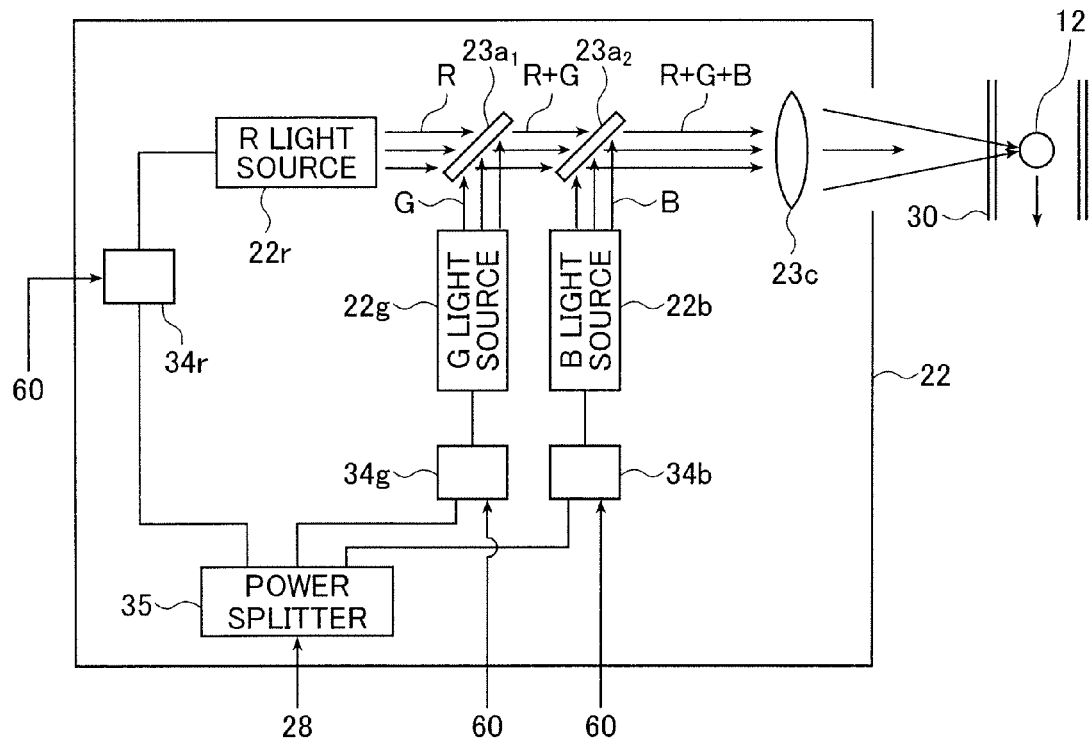
FIG. 2 is a schematic structural diagram showing an example of laser light sources that are used in the fluorescence detecting device outputting an intensity-modulated laser beam according to the present invention.

FIG. 2 is a diagram showing an example of the configuration of the laser light source section 22.

The laser light source section 22 is a section that outputs the laser beam having a wavelength of a visible band of 350 nm to 800 nm, modulated in intensity and modulated in coding.

The laser light source section 22 has an R light source 22r, a G light source 22g, and a B light source 22b. The R light source 22r mainly emits a red laser beam R as a CW (continuous wave) laser beam that is constant in intensity, and also intermittently outputs the laser beam R while modulating the intensity of the CW laser beam at a given frequency. The G light source 22g emits a green laser beam G as a CW laser beam that is constant in intensity, and also intermittently outputs the laser beam G while modulating the intensity of the CW laser beam at a given frequency. The B light source 22b emits a blue laser beam B as a CW laser beam that is constant in intensity, and also intermittently outputs the laser beam B while modulating the intensity of the CW laser beam at a given frequency.

Further, the laser light source section 22 includes dichroic mirrors $23a_1$, $23a_2$, a lens system 23c that focuses a laser beam consisting of the laser beams R, G, and B on a measurement point in the tube 30, laser drivers 34r, 34g, and 34b that drive the R light source 22r, the G light source 22g, and the B light source 22b, respectively, and a power splitter 35 that distributes the supplied signal to the laser drivers 34r, 34g, and 34b, respectively.

The laser light sources that output those laser beams can be formed of, for example, a semiconductor laser. The laser beam has an output of, for example, about 5 to 100 mW. On the other hand, the frequency (modulation frequency) that modulates the intensity of the laser beam, which is slightly longer in the cycle time than the fluorescence relaxation time is, for example, 10 to 100 MHz.

The dichroic mirror $23a_1$ is a mirror that transmits the laser beam R and reflects the laser beam G, and the dichroic mirror $23a_2$ is a mirror that transmits the laser beams R and G, and reflects the laser beam B.

With the above configuration, the laser beams R, G, and B are combined together into an irradiation beam with which the specimen 12 is irradiated at the measurement point.

The laser drivers 34r, 34g, and 34b are connected to the control/processing section 28, and configured in such a manner that the intensity of the output of the laser beams R, G, and B, and the on/off operation of the output thereof are controlled. In this example, the respective laser beams R, G, and B are modulated in intensity at a given frequency and the on/off operation of the output is controlled according to a modulation signal and a pulse modulation signal, as will be described later.

The R light source 22r, the G light source 22g, and the B light source 22b oscillate and emits at predetermined wavelength bands in such a manner that the laser beams R, G, and B excite the fluorochromes so as to generate fluorescence having specific wavelength bands. The fluorochromes that are excited by the laser beams R, G, and B are adhered to the specimen 12 such as a biologic material or micro beads to be measured in fluorochrome, and when the specimen 12 passes through the tube 30 as the object to be measured, the fluorochromes generate fluorescence at specific wavelengths upon receiving the irradiation of the laser beams R, G, and B at the measurement point.

Figure 3:
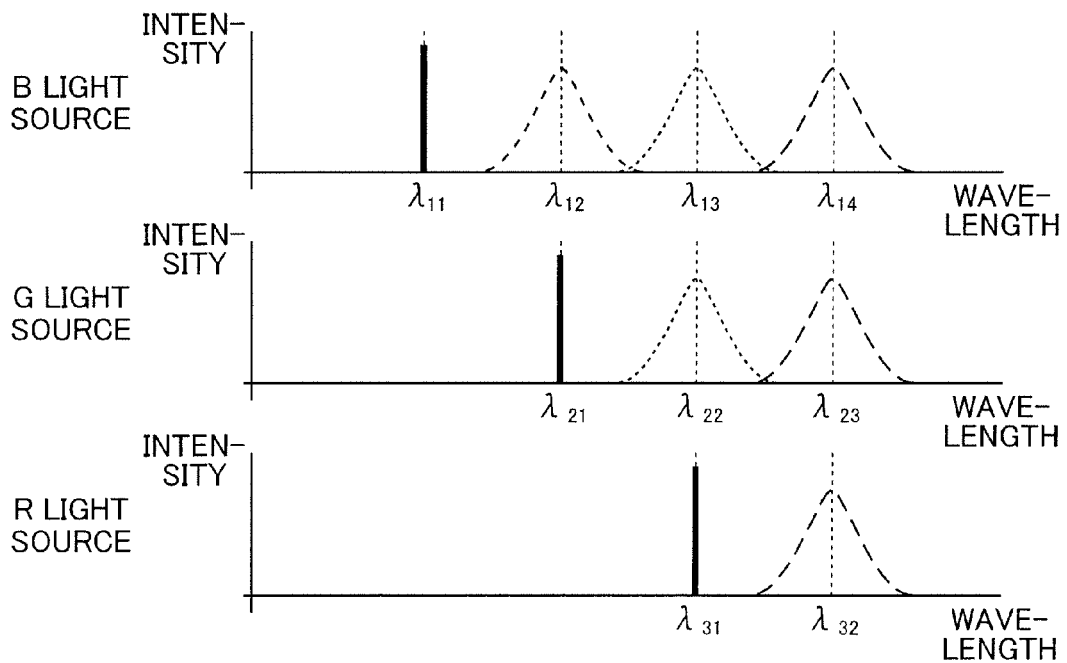
FIG. 3 are graphs each schematically showing a spectrum intensity distribution of a laser beam that is output from the laser light sources shown in FIG. 2 and light that is generated by a fluorochrome.

FIG. 3 is a diagram schematically showing the emitting wavelength of the laser beam, and the spectrum intensity distribution of fluorescence that is generated by the fluorochrome by using the laser beam. For example, three kinds of fluorescence consisting of fluorescence having a center wavelength of $\lambda_{12}$, fluorescence having a center wavelength of $\lambda_{13}$, and fluorescence having a center wavelength of $\lambda_{14}$ are generated by three different fluorochromes by irradiation of the laser beam having a wavelength $\lambda_{11}$ which is output from the B light source. Likewise, two kinds of fluorescence ($\lambda_{22}$, $\lambda_{23}$) are generated by irradiation of the laser beam having a wavelength $\lambda_{21}$ that is output from the G light source. Further, one kind of fluorescence ($\lambda_{32}$) is generated by irradiation of the laser beam having a wavelength $\lambda_{31}$ that is output from the B light source.

The light receiving section 24 is so arranged as to face the laser light source section 22 with the tube 30 provided therebetween. The light receiving section 24 is equipped with a photoelectric converter that outputs a detection signal indicating that the specimen 12 passes by the measurement point when the laser beam is scattered forward by the specimen 12 that passes by the measurement point. The signal that is output from the light receiving section 24 is supplied to the control/processing section 28, and used as a trigger signal that announces a timing at which the specimen 12 is passing by the measurement point in the tube 30 in the control/processing section 28.

On the other hand, the light receiving section 26 is so arranged as to be perpendicular to the output direction of the laser beam that is output from the laser light source section 22 and also perpendicular to the moving direction of the specimen 12 in the tube 30. The light receiving section 26 is equipped with photoelectric converters that receives the fluorescence that is generated by the specimen 12 that has been irradiated at the measurement point.

Figure 4:
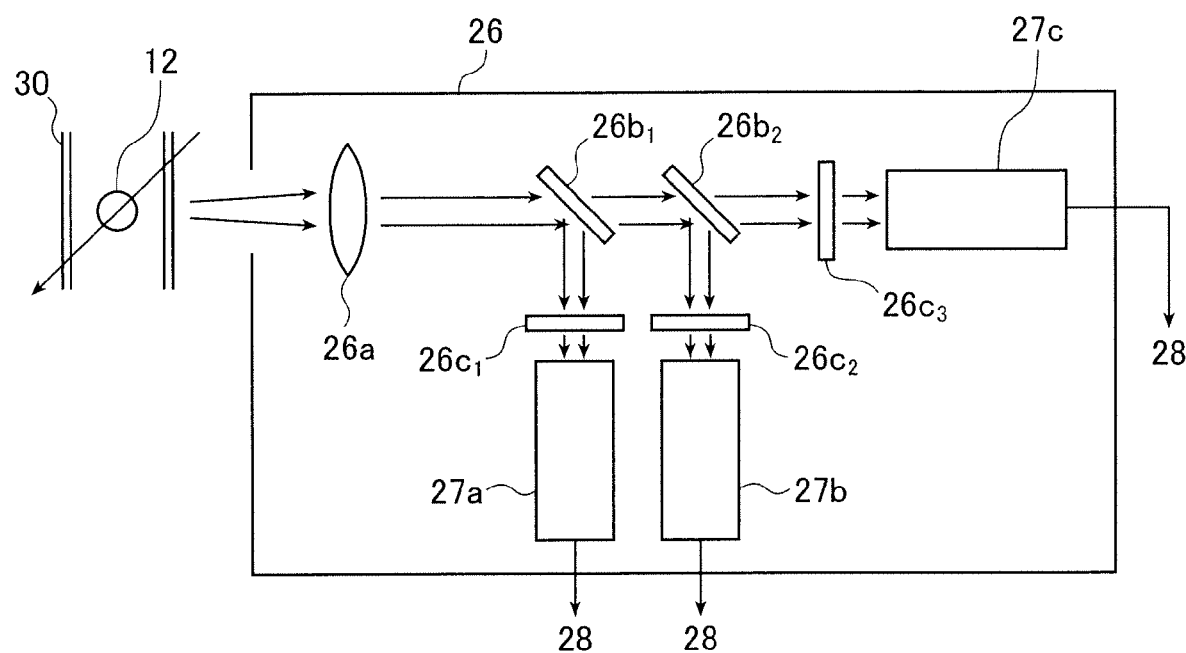
FIG. 4 is a schematic structural diagram showing an example of a light receiving section that is used in the fluorescence detecting device outputting an intensity-modulated laser beam according to the present invention.

FIG. 4 is a schematic structural diagram showing the configuration of an example of the light receiving section 26.

The light receiving section 26 shown in FIG. 4 includes a lens system 26a that focuses the fluorescence signal from the specimen 12, dichroic mirrors $26b_1$ and $26b_2$, band pass filters $26c_1$ to $26c_3$, and photoelectric converters 27a to 27c such as photoelectron multiple tubes.

The lens system 26a is so designed as to focus the fluorescence that has been input to the light receiving section 26 on the light receiving surface of the photoelectric converters 27a to 27c. The dichroic mirrors $26b_1$ and $26b_2$ are mirrors that reflect the fluorescence having given wavelength bands and transmit other fluorescence. The reflection wavelength bands and the transmission wavelength bands of the dichroic mirrors $26b_1$ and $26b_2$ are set so that through filtering the fluorescence by the band pass filters $26c_1$ to $26c_3$, the fluorescence having the predetermined wavelength bands are taken in by the photoelectric converters 27a to 27c.

The band pass filters $26c_1$ to $26c_3$ are filters that are disposed in front of the light receiving surfaces of the respective photoelectric converters 27a to 27c, and transmit only the fluorescence of the given wavelength bands. The wavelength bands of the transmitted fluorescence are set in correspondence with the wavelength band of the fluorescence that is generated by the fluorochromes shown in FIG. 2. For example, the wavelength band of the transmitted fluorescence is a band of a constant wavelength width centered on the wavelength $\lambda_{13}$ which is generated by the irradiation of the laser beam of the wavelength $\lambda_{11}$ which is generated from the B laser beam. In this case, as shown in FIG. 3, because the fluorescence centered on the wavelength $\lambda_{22}$ which is generated by irradiation of the laser beam having the wavelength $\lambda_{21}$ which has been output from the G light source has a center wavelength in the vicinity of the wavelength $\lambda_{13}$, the band pass filter transmits the above fluorescence together with the fluorescence centered on the wavelength $\lambda_{13}$. However, the fluorescence having the wavelength $\lambda_{21}$ as the center wavelength and the fluorescence having the wavelength $\lambda_{13}$ as the center wavelength are received by the photoelectric converters 27a to 27c as the fluorescence having signal information that has been modulated by a coding sequence signal (codes 1 to 3 of FIG. 7) which will be described later. In other words, signal processing that will be described later is conducted on the fluorescence signal that is received and generated, thereby making it possible to identify which laser beam generates the signal fluorescence.

Each of the photoelectric converters 27a to 27c is formed of, for example, a sensor having a photoelectron multiple tube, which converts a light that has been received by the photoelectric surface into an electric signal. In this example, since the received fluorescence is received as an optical signal having the signal information, the output electric signal is the fluorescence signal having the signal information. The fluorescence signal is amplified by an amplifier and then supplied to the control/processing section 28.

Figure 5:
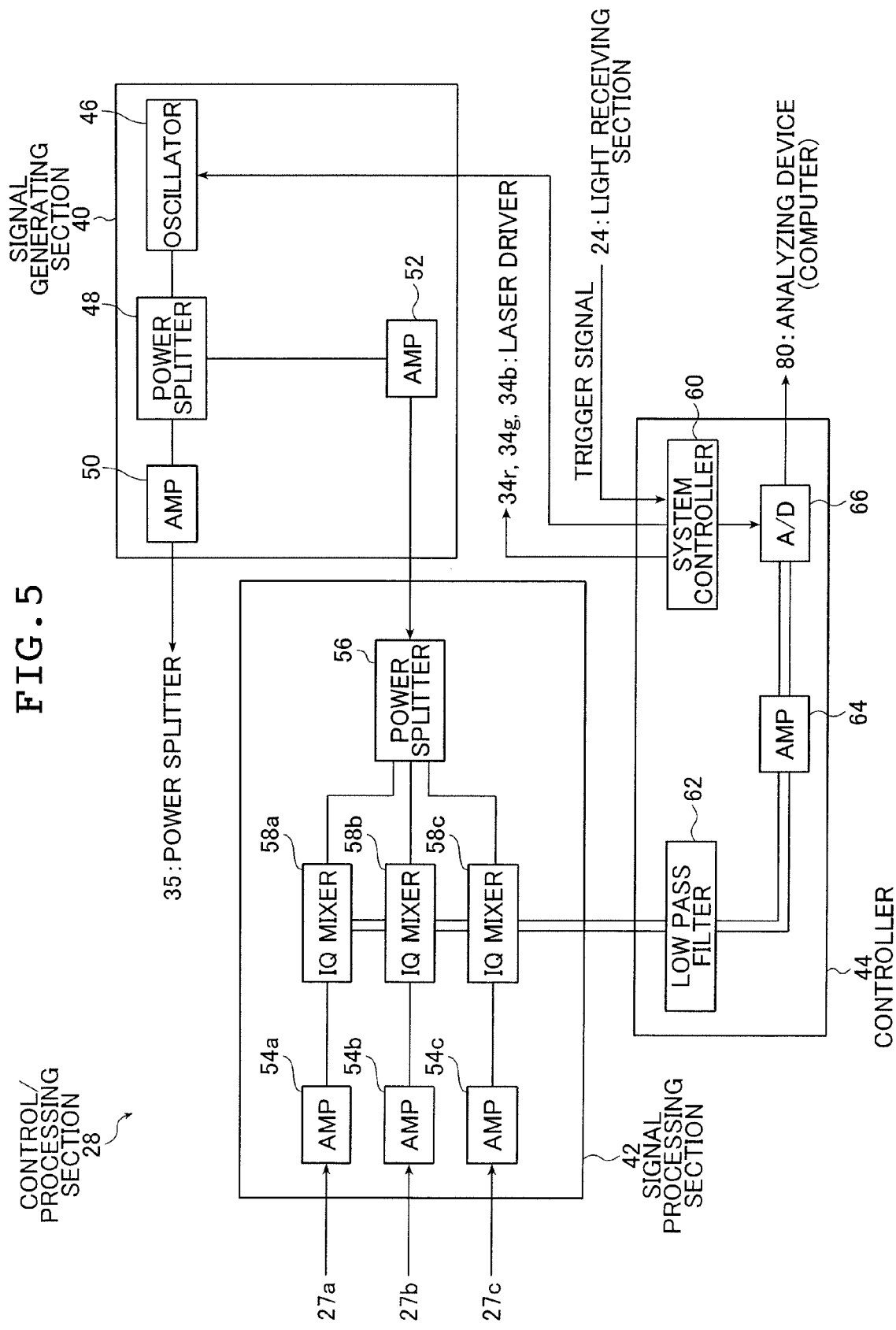
FIG. 5 is a schematic structural diagram showing an example of a control/processing section that is used in the fluorescence detecting device outputting an intensity-modulated laser beam according to the present invention.

As shown in FIG. 5, the control/processing section 28 includes a signal generating section 40, a signal processing section 42, and a controller 44. The signal generating section 40 and the controller 44 constitute a light source control section that generates a modulation signal having a given frequency. The signal generating section 40 is a section that generates a modulation signal for modulating (amplitude modulating) the intensity of the laser beam at a given frequency. More specifically, the signal generating section 40 includes an oscillator 46, a power splitter 48, and amplifiers 50 and 52. The signal generating section 40 supplies the generated modulation signal to the power splitter 35 of the laser light source 22 and also to the signal processing section 42. The reason that the modulation signal is supplied to the signal processing section 42 is because the modulation signal is used as a reference signal for detecting the fluorescence signals that are output from the photoelectric converters 27a to 27c as described below. The modulation signal is a sine wave signal of a given frequency, and set to a frequency ranging from 10 to 100 MHz.

The signal processing section 42 is a section that extracts information related to the phase delay of the fluorescence that is generated from the micro beads by irradiation of the laser beam, by using the fluorescence signal that is output from the photoelectric converters 27a to 27c. The signal processing section 42 includes amplifiers 54a to 54c that amplify the fluorescence signals that are output from the photoelectric converters 27a to 27c, a power splitter 56 that splits a modulation signal that is a sine wave signal supplied from the signal generating section 40 to the respective amplified fluorescence signals, and IQ mixers 58a to 58c that mix the modulation signal as the reference signal with the amplified fluorescence signals.

Figure 6:
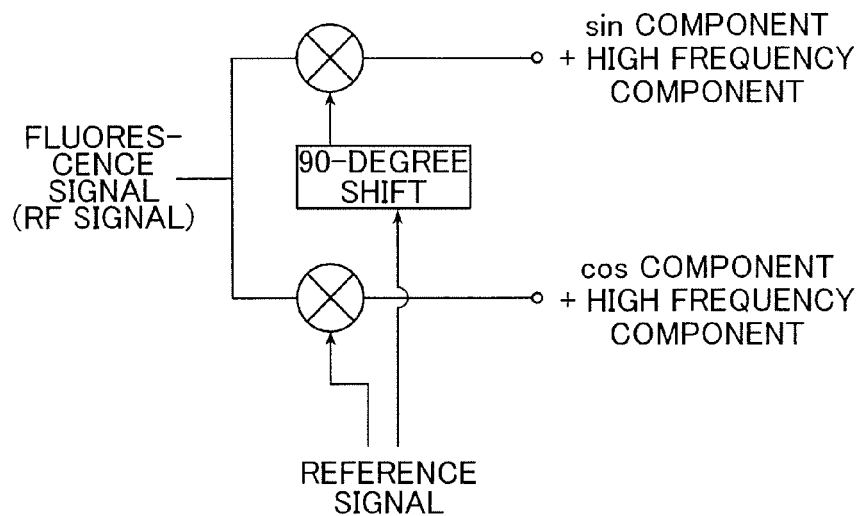
FIG. 6 is a diagram for explaining an IQ mixer in the control/processing section shown in FIG. 5.

The IQ mixers 58a to 58c are devices that mix the fluorescence signals that are supplied from the photoelectric converters 27a to 27c with the reference signal that is the modulation signal which is supplied from the signal processing section 40. More specifically, as shown in FIG. 6, each of the IQ mixers 58a to 58c multiplies the reference signal by the fluorescence signal (RF signal) to calculate a processing signal including the cos component and high frequency component of the fluorescence signal. Further, the IQ mixer multiplies a signal obtained by shifting the phase of the reference signal by 90 degrees by the fluorescence signal to calculate a processing signal including the sin component and the high frequency component of the fluorescence signal. The processing signal including the cos component and the processing signal including the sin component are supplied to the controller 44.

The controller 44 is a section that controls the signal generating section 40 so as to generate a sine wave signal having a given frequency. The controller 44 also controls the on/off operation of the output of the laser beam of the laser drivers 34r, 34g, and 34b in the laser light source section 22 by using the coding sequence signal. The controller 44 further removes the high frequency component from the processing signals including the cos component and the sin component of the fluorescence signal that has been obtained by the signal process section 42 to obtain the cos component and the sin component of the fluorescence signal.

More specifically, the controller 44 has a system controller 60, a low pass filter 62, an amplifier 64, and an A/D converter 66.

The system controller 60 gives instructions for controlling the operation of the respective sections, and manages the entire operation of the flow cytometer 10. The low pass filter 62 removes the high frequency component from the processing signals which are combinations of the high frequency component and the cos component, the sin component that have been calculated by the signal processing section 42. The amplifier 64 amplifies the processing signal of the cos component and the sin component from which the high frequency component has been removed. The A/D converter 66 samples the amplified processing signal. More specifically, the system controller 60 determines the oscillation frequency of the oscillator 46 in order to modify the intensity of the laser beam. In addition, the system controller 60 generates the pulse control signal that controls the on/off operation of the output of the laser beam. The pulse control signal is produced by one coding sequence signal that is selected from plural coding sequence signals that are orthogonal to each other. The coding sequence signal is constituted by signal values of one bit, and is coded by the bit number of a given code length.

Hereinafter, the coding sequence signal will be described.

The controller 44 generates the coding sequence signal that is a reference by using a sequence code $C=\{a_0, a_1, a_2, \ldots, a_{N-1}\}$ (N is a natural number representative of a code length). The controller 44 also generates the coding sequence signal by using a sequence code $T_{q1} \cdot c$ ($T_{q1}$ is an operator that is shifted by q1 bit in a higher bit direction) which is obtained by shifting the sequence code C by q1 bits in the higher bit direction. In this example, the sequence code $T_{q1} \cdot C$ is $\{a_{q1}, a_{q1+1}, a_{q1+2}, \ldots, a_{q1+N-1}\}$. Further, the controller 44 generates the coding sequence signal by using the sequence code $T_{q2} \cdot C$ that is obtained by shifting the sequence code C by q2 bits (for example, q2=2×q1) in the higher bit direction.

Since the sequence codes C, $T_{q1} \cdot C$, $T_{q2} \cdot C$ which are used to generate the coding sequence signal have the characteristic orthogonal to each other, the generated coding sequence signals are also orthogonal to each other.

As an example of the sequence code C, as indicated below, there is a PN sequence (pseudorandom noise sequence) that is coded by using, for example, a coefficient $h_j$ (j=an integer of 1 to 8) and an initial value $a_k$ (k is an integer of 0 to 7). The PN sequence can be defined by, for example, the following formula (1). In the formula (1), the order is eighth order. In the formula, N is the code length of the sequence code, and for example, N=255 ($=2^8-1$) bits are set.

[EX. 1]

$$h_1 = 0, h_2 = 1, h_3 = 1, h_4 = 1, h_5 = 0, h_6 = 0, h_7 = 0, h_8 = 1, \quad (1)$$
$$a_0 = 0, a_1 = 0, a_2 = 0, a_3 = 0, a_4 = 0, a_5 = 0, a_6 = 0, a_7 = 1$$
$$a_{8+i} = \sum_{j=1}^{8} h_j a_{8-j+i} (i = 0, 1, 2, \ldots)(\bmod 2)$$

In the case where the sequence code C is the PN sequence code, since the code length is a cyclic code of N, $a_N=a_0$, $a_{N+1}=a_1, \ldots$. Further, when another sequence code having the same code length as that of the sequence code C is set as $C'=\{b_0, b_1, b_2, \ldots, b_{N-1}\}$, and the above operator $T_q$ is set as a sequence code $T_q \cdot C'=\{b_q, b_{q+1}, b_{q+2}, \ldots, b_{q+N-1}\}$ acting on the sequence code C', a mutual correlation function $R_{cc'}(q)$ between the sequence codes C and C' is defined as the following formula (2). In this formula, $N_A$ is the number in which a term $a_i$ and a term $b_{q+i}$ (i is an integer that is equal to or more than 0 and equal to or less than N−1) in the sequence code coincide with each other, and $N_D$ is the number in which the term $a_i$ and the term $b_{q+i}$ in the sequence code does not coincide with each other. Further, the sum of $N_A$ and $N_D$ is the code length N ($N_A+N_D=N$). In this formula, i and q+i are considered in mod(N).

[EX. 2]

$$R_{cc'}(q) = \frac{N_A - N_D}{N_A + N_D} \quad (2)$$

A result of adding two sequence codes in mod (2) in each of the terms in the above PN sequence characteristically becomes a PN sequence obtained by cyclically shifting the original PN sequence, and the number in which the value of the PN sequence is zero is smaller by 1 than the number in which the value is 1, so that $N_A-N_D=-1$. As a result, the values represented by the following formulae (3) and (4) are expressed in the PN sequence.

[EX. 3]

$$R_{cc'}(q)=1\{q=0(\bmod N)\} \quad (3)$$

[EX. 4]

$$R_{cc'}(q)=-1/N\{q \neq 0(\bmod N)\} \quad (4)$$

In the case where the bit shift quantity is 0, that is, q=0 in the above formula (3), a value of $R_{cc'}(q)$ is 1 as represented by formula (3), and there is provided self-correlation. On the other hand, in the case where the bit shift quantity is not 0, that is, q>0, $R_{cc'}(q)$ becomes −(1/N) as represented by formula (4). In this expression, when the code length N is increased, a value of $R_{cc'}(q)$ (q>0) approaches 0. In other words, the sequence codes C and C' have self-correlativity and orthogonality.

The above sequence code having self-correlativity and orthogonality is used to generate the coding sequence signal consisting of binary values having a value of 0 and a value of 1.

Figure 7A:
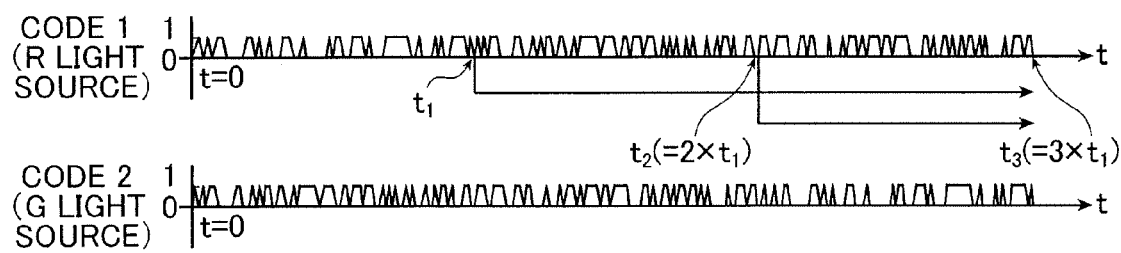
FIGS. 7A and 7B are diagrams showing an example of respective signals that are generated by the fluorescence detecting device outputting an intensity-modulated laser beam according to the present invention.

FIG. 7A shows an example of the generated coding sequence signal. The coding sequence signal of a code 1 is a signal having a code length of N=255 bits, and a product of the code length N and a time resolved width Δt is a time length from times 0 to $t_3$ of FIG. 7A. The on/off operation of output of the laser light source is intermittently controlled in such a manner that the laser beam is output when the value is 1, and the laser beam is not output when the value is 0 in the above signal.

In this example, in the coding sequence signal, a signal at a time 0 in a code 2 is generated in correspondence with a signal at a time $t_1$ in a code 1, and a signal after the time 0 in the code 2 is generated in correspondence with a signal after the time $t_1$ in the code 1. Likewise, in the coding sequence signal, a signal at the time 0 in a code 3 is generated in correspondence with a signal at a time $t_2$ (for example, $t_2=2×t_1$) in the code 1, and a signal after the time 0 in the code 3 is generated in correspondence with a signal after the time $t_2$ in the code 1.

A light source control section 28a cyclically and repetitively generates those signals, and is configured so that the code 1 is supplied to the laser driver 34r, the code 2 is supplied to the laser driver 34g, and the code 3 is supplied to the laser driver 34b, as pulse control signals, respectively.

The coding sequence signals in the present invention are generated by using the sequence code of the above PN sequence. However, the generation of the coding sequence signal having self-correlativity and orthogonality in the present invention is not limited to the above method, and any methods can be applied so far as the coding sequence signal having self-correlativity and orthogonality is generated.

Figure 7B:
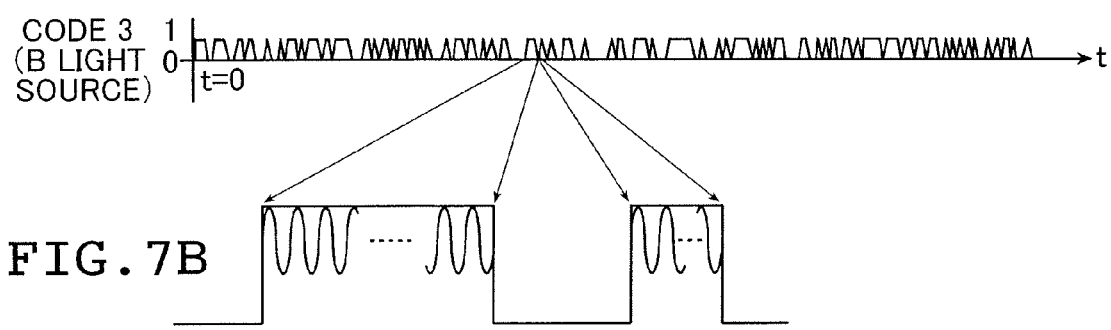

FIG. 7B shows an association between the pulse modulation due to the coding sequence signal and the intensity modulation due to the frequency of the laser beam. In the case where the laser beam is on due to the pulse modulation, the laser beam is so modulated as to vibrate in intensity in a cycle shorter than at least a time of the on-state.

The system controller 60 of the controller 44 generates the coding sequence signal by using the sequence code as shown in FIG. 7A, and supplies the coding sequence signal to the respective laser drivers 34r, 34g, and 34b as a pulse control signal that controls the on/off operation of output of the laser beam.

It is preferable that, in the sampling in the A/D converter 66 of the controller 44, the time resolution width (sampling interval) of sampling be made to correspond to the time resolution width of the coding sequence signal in order to efficiently calculate the correlation function between the coding sequence signal and the fluorescence signal as will be described below. For example, when the time resolution width of the coding sequence signal is 0.5 microsec, it is preferable that the time resolution width of sampling of the fluorescence signal be also set to 0.5 microsec or 1/integer of 0.5 microsec.

The analyzing device 80 is a device that obtains a phase delay angle with respect to the laser beam of fluorescence, also obtains a fluorescence relaxation time constant (=fluorescence relaxation time) from the phase delay angle, and specifies which laser beam's irradiation causes the fluorescence signal that has been output from the light receiving section 26. The analyzing device 80 is a processor section that is formed of a computer and calculates a fluorescence relaxation time (=fluorescence relaxation time constant) of the present invention.

The processing signal including the cos component and the sin component of the fluorescence signal includes also information on the coding sequence signal. Therefore, the analyzing device 80 first conducts coding identification conversion using self-correlativity and orthogonality of the processing signal, and extracts the values of the cos component and the sin component of the fluorescence signal in each of the laser beams. The analyzing device 80 obtains the phase delay angle with respect to the laser beam of fluorescence by using the cos component and the sin component. The analyzing device 80 obtains the fluorescence relaxation time constant (fluorescence relaxation time) according to the phase delay angle, and identifies the fluorochrome, thereby specifying the kind of specimen 12. Further, the analyzing device 80 is informed of the coding sequence signal used in the coding identification conversion, to thereby specify which laser beam's irradiation causes the fluorescence signal.

The obtained phase shift angle depends on the fluorescence relaxation time constant of fluorescence that is generated by the fluorochrome. In the case where the phase shift angle is represented by, for example, a first order lag relaxation process, the cos component and the sin component are expressed by the following formulae (5) and (6).

[EX. 5]

$$\cos(\theta) = \frac{1}{\sqrt{1+(\omega\tau)^2}} \quad (5)$$

-continued

[EX. 6]

$$\sin(\theta) = \frac{\omega\tau}{\sqrt{1+(\omega\tau)^2}} \quad (6)$$

Figure 8:
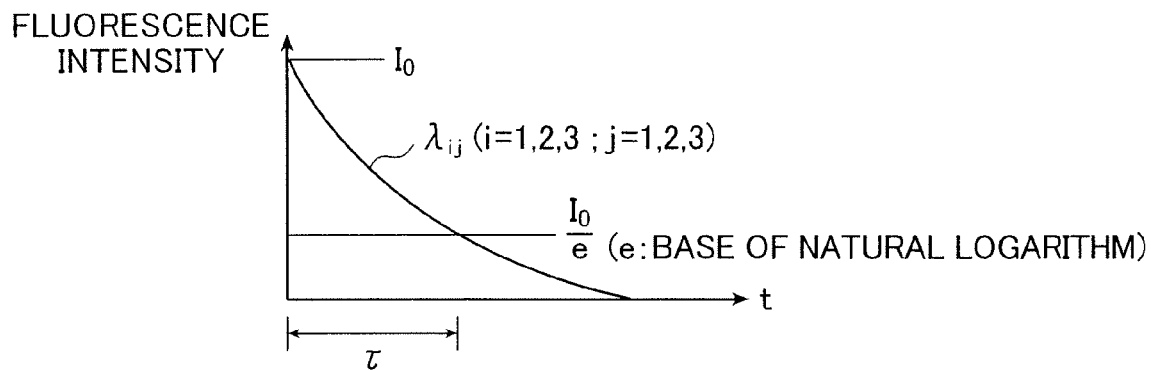
FIG. 8 is a diagram for explaining characteristics of a fluorescence intensity of light that is generated by the fluorochrome.

In the expressions, $\theta$ is the phase shift angle, $\omega$ is the modulation frequency of the laser beam, and $\tau$ is the fluorescence relaxation time constant. When it is assumed that the initial fluorescence intensity is $I_0$ as shown in FIG. 8, the fluorescence relaxation time constant $\tau$ is a period of time from initial time point to a time point where the fluorescence intensity becomes $I_0/e$ (e is a base of natural logarithm, e≈2.71828).

The analyzing device 80 obtains the phase shift angle $\theta$ according to the ratio $\tan(\theta)$ of the cos component and the sin component of the fluorescence signal, and can obtain the fluorescence relaxation time constant $\tau$ from the above formulae (5) and (6) by using the phase shift angle $\theta$. As described above, the fluorescence relaxation time constant $\tau$ depends on the kind of fluorochrome. Further, when two kinds of fluorochromes are mixed with each other at a different ratio, an apparent fluorescence relaxation time constant $\tau$ also changes according to the ratio. Thus, the analyzing device 80 obtains the fluorescence relaxation time constant $\tau$, thereby enabling the ratio of those two fluorochromes to be specified.

As described above, the analyzing device 80 irradiates the fluorescence detection micro beads with the intensity-modulated laser beam, and detects the fluorescence that is generated at that time, thereby making it possible to identify the kind of generated fluorescence. As a result, it is possible to specify the kind of specimen 12 such as the micro beads.

A signal of fluorescence that is generated by the fluorochrome in the specimen 12 is a fluorescence signal that is caused by the laser beam that has been modulated (output is controlled) according to the known coding sequence signal which has been generated by the system controller 60. Thus, the fluorescence signal is also a signal whose optical intensity has been modulated according to the coding sequence signal that has been generated by the system controller 60. Accordingly, the analyzing device 80 synchronizes the code (coding sequence signal) that is an input signal generated by the system controller 60 with the fluorescence signal that is a response signal, and investigates the correlation function, thereby making it possible to determine which code has been used to modulate the laser beam that has caused the fluorescence signal included in the fluorescence signal. In other words, in the case where the analyzing device 80 calculates the correlation function between the code that has been generated by the system controller 60 and the fluorescence signal and the code is found to have a high correlation value with respect to the fluorescence signal, the fluorescence signal generated by the laser beam which has been modulated by the code (coding sequence signal) is included. On the other hand, in the case where the code is found to have extremely low or zero correlation, the fluorescence signal generated by the laser beam that has been modulated by the code is not included. Accordingly, the laser beam that has been modulated by the different code in each of the laser light sources is output, thereby making it possible to determine which laser beam causes the received fluorescence.

The analyzing device 80 repetitively averages the correlation function between the code that is an input signal and the fluorescence signal that is a response signal according to the cycle of circulating codes to obtain a stable value. The analyzing device 80 specifies which laser beam causes the received fluorescence. Further, since the wavelength bands of the laser beams that have been received by the respective photoelectric converters 27a to 27c are known, the analyzing device 80 is capable of specifying the kind of fluorescence.

As described above, the analyzing device 80 is capable of identifying and specifying by irradiation of which laser beam and in which wavelength band the fluorochrome in the specimen 12 includes the signal of fluorescence that has been radiated.

As described above, the analyzing device 80 specifies the fluorochrome disposed in the specimen 12 such as the micro beads by using the fluorescence relaxation time constant of fluorescence generated by the fluorochrome and information indicating which laser beam causes the fluorescence signal, thereby making it possible to specify the kind of specimen 12 that passes by the tube 30. In the case of the micro beads, since, for example, a given DNA fragment is provided on corresponding with the fluorochrome of the micro beads, the fluorochrome is specified, to thereby enable the kind of DNA fragment on the micro beads to be notified of. As a result, in the case where the analyzing device 30 measures the fluorescence of the micro beads and the fluorescence of the DNA fragment of an object to be detected at the same time, the analyzing device 30 determines that the DNA fragment of the object to be detected acts on a specific DNA fragment of the micro beads, to conduct the biological coupling therewith. In this way, the analyzing device 80 is capable of analyzing which micro beads the DNA fragment of the object to be detected is coupled with.

In the above manner, the analyzing device 80 obtains the histogram of the kind or the various characteristics of biologic material in the specimen 12 in a short time.

The flow cytometer 10 is configured as described above.

The signal processing device 20 of the flow cytometer 10 thus configured allows the signal of a given frequency to be generated in the oscillator 46 according to an instruction from the controller 44, the signal to be amplified by the amplifier 50, and the signal to be supplied to the laser light source section 22 and the signal processing section 42. In this state, the specimen 12 flows in the tube 30 to form a flow. The flow has, for example, a flow rate of 1 to 10 m/sec in the flow path diameter of 100 μm. Further, in a case where the micro beads are used as the specimen 12, the spherical diameter of the micro beads is several μm to 30 μm.

When the measurement point is irradiated with the laser beam, a detection signal that detects the pass of the specimen 12 by the light receiving section 24 is output to the controller 44 as a trigger signal.

The controller 44 deals with the detection signal as the trigger signal, and generates the coding sequence signal having self-correlativity and orthogonality to another coding sequence signal simultaneously with the trigger signal output. The coding sequence signal is cyclically and repetitively generated. The coding sequence signal is supplied to the laser drivers 34r, 34g, and 34b in order to be used as a pulse control signal that controls the on/off operation of the output of the laser beam from the laser light source section 22.

In the laser light source section 22, the on/off operation of the output of each laser beam is controlled according to the pulse control signal to generate the laser beam having the signal information of the pulse modulation according to the coding sequence signal. The laser beam is used to excite the fluorochrome in the specimen 12 which passes by the measurement point. The fluorochrome generates fluorescence by irradiation of the laser beam. The fluorescence generated by the fluorochrome is received by the light receiving section 26. The laser beam whose output is on is modulated in intensity at a given frequency.

The fluorescence from the fluorochrome which is generated by irradiation of the above laser beam is modulated in intensity at the given frequency with a phase delay angle, and the fluorescence that is excited and generated according to the on/off operation of the laser beam is also an on/off signal.

A period of time from the detection by the light receiving section 24 of the specimen 12 passing by to the irradiation of the modulated laser beam as described above is extremely short. The specimen 12 is irradiated with the laser beam whose on/off operation is controlled according to the coding sequence signal that is cyclically repeated while the laser beam is modified in the amplitude at the given frequency during several μsec to several tens μsec during which the specimen 12 passes by the measurement point.

In this example, the modulation frequency of the laser beam is, for example, 10 to 100 MHz. Further, in the case where the coding sequence signal is generated, for example, with the time resolution width of 1 μsec and when the code length N of the coding modulation signal is 7 bits, the coding sequence signal is repetitively and cyclically generated with 7 μsec (=1.0×7) as one cycle. The laser beam is modulated on the basis of the coding sequence signal that is repetitively generated. Accordingly, the laser beam has the coding sequence signal with 7 μsec as one cycle circulated several times to several tens times during several μsec to several tens μsec.

The fluorescence signals that are received and output by the photoelectric converters 27a to 27c of the light receiving section 26 are amplified by the amplifiers 54a to 54c, and then mixed with the modulation signal that is a sine wave signal that has been supplied from the signal generating section 40 by means of the IQ mixers 58a to 58c.

The IQ mixers 58a to 58c generates a mixed signal resulting from multiplying the modulation signal (reference signal) that is the sine wave signal by the fluorescence signal. The IQ mixers 58a to 58c also generate a mixed signal resulting from multiplying the signal that is shifted in phase from the modulation signal (reference signal) that is the sine wave signal by 90 degrees by the fluorescence signal.

Subsequently, those generated two mixed signals are transmitted to the low pass filter 62 of the controller 44, and the high frequency components are removed from those mixed signals to extract the signal having the cos component and the sin component of the fluorescence signal. The signal having the cos component and the sin component of the fluorescence signal is amplified, subjected to A/D conversion, and then transmitted to the analyzing device 80. The A/D conversion is synchronized with a timing of the trigger signal from the light receiving section 24, and the fluorescence signal is sampled with the same time resolution width as the time resolution width Δt of the coding sequence signal. The sampling is, for example, a 16 bits sampling (sampling of the gradation of 0 to ±32767). The fluorescence signal is generated by the laser beam that has been modulated in pulse according to the coding sequence signal. Thus, the sampled data which is obtained from the fluorescence signal includes information on the coding sequence signal.

For example, the intensity amplitude $A_i(t)$ of the time modulated laser beam that is output from the i-th (i=natural number of 1 to 3) laser light source section 22 is described as the following formulae (7) ($p_i(t)$ is a time modulated component of the PN coding modulation signal, ω is a modulation frequency), and a reference signal (modulation signal) $A_0(t)$ that is supplied to the IQ mixers 58a to 58c is described as the following formula (8). In this case, a signal $A_{90}(t)$ that is shifted in phase from the modulation signal (reference signal) that is a sine wave signal by 90 degrees, which is used in each of the IQ mixers 58a to 58c, is described as the following formula (9). On the other hand, when the amplitude of the fluorescence signal is described according to the following formula (10), the mixed signals at the IQ mixers 58a to 58c are represented by the following formula (11). The higher order components of those two mixed signals are removed by using the low pass filter 62, and is then subjected to A/D conversion to produce digital signals.

[EX. 7]

$$A_i(t) = p_i(t) \cdot \cos(\omega t) \ (i=1, 2, 3) \quad (7)$$

[EX. 8]

$$A_0(t) = \cos(\omega t) \quad (8)$$

[EX. 9]

$$A_{90}(t) = -\sin(\omega t) \quad (9)$$

[EX. 10]

$$A(t) = \sum_{i=1}^{3} p_i(t) \cdot r_i \cdot \cos(\omega t + \theta_i) \quad (10)$$

($r_i$ is the intensity amplitude of fluorescence)

[EX. 11]

$$\text{mixed signal} = \begin{cases} \dfrac{1}{2} \sum_{i=1}^{3} p_i(t) \cdot r_i \cdot \cos\theta_i + \text{(higher order component)} \\ \dfrac{1}{2} \sum_{i=1}^{3} p_i(t) \cdot r_i \cdot \sin\theta_i + \text{(higher order component)} \end{cases} \quad (11)$$

The coding sequence signal used in the time modulation of the laser beam has the self-correlation, and has orthogonality with respect to another coding sequence signal. Accordingly, a correlation between the coding sequence signal and the digital signal that has been subjected to A/D conversion is calculated to conduct coding identification conversion that decomposes the digital signal in each of the laser signals. That is, $1/2 \cdot r_i \cdot \cos(\theta i)$ and $1/2 \cdot r_i \cdot \sin(\theta i)$ in the formula (11) are obtained through the coding identification conversion. In this expression, $\theta i$ represents the phase delay angle of the fluorescence that is generated by the laser beam which is output from the i-th laser light source section 22 with respect to the laser beam. Therefore, $\tan(\theta i)$ can be obtained by using the values of $1/2 \cdot r_i \cdot \cos(\theta i)$ and $1/2 \cdot r_i \cdot \sin(\theta i)$. The fluorescence relaxation time constant r is obtained by using the value of $\tan(\theta i)$ and the above-mentioned formulae (5) and (6).

The fluorescence relaxation time constant τ depends on the fluorochrome, therefore by using a different kind of fluorochrome for a different kind of specimen 12 such as the micro beads (kind of biologic material adhered to the specimen 12 is different), the kind of fluorochrome can be specified. As a result, the kind of specimen 12 can be specified. Accordingly, the kind of specimen 12 is specified by the fluorescence that is generated by the specimen 12. In the case of additionally detecting the fluorescence that is generated by the biologic material having a given fluorochrome, it is possible to specify which kind of specimen 12's structure the biologic material is biologically coupled with. The analysis can be conducted by using those results.

In particular, when two different kinds of fluorochromes are mixed together at different ratios, the apparent fluorescence relaxation time constant τ also changes according to the ratio. Thus, the mixture ratio is changed, thereby making it possible to set an extremely large number of fluorescence relaxation time constants. Accordingly, it is possible to set a variety of micro beads which are capable of identifying the generated fluorescence by using the fluorochromes having different fluorescence relaxation time constants for each kind of the micro beads.

In addition, since the coding sequence signal having the self-correlation can be given in conducting the above coding identification conversion, it is possible to specify which laser beam causes the fluorescence signal. In the conventional art, since the laser beam is not modulated and the modulated signal information is not included in the fluorescence, it is impossible to specify which laser beam excites the fluorescence.

In the present invention, even if the fluorescence is emitted at the same wavelength, the coding sequence signal of the laser beam used for excitation is changed, thereby making it possible to receive the fluorescence as a different fluorescence signal. As a result, it is possible to specify a large number of laser beams that are used for excitation of the fluorochrome in a short time by using a large number of coding sequence signals having orthogonality. Accordingly, even if there are a large number of fluorochromes that are close to each other in the wavelength band of fluorescence, or even if a large number of laser beams are bundled together and irradiated at once, the signal information of the irradiated laser beam is included in the fluorescence. It is possible to specify the fluorochrome that is adhered to the specimen so far as the signal information in the light receiving signal can be identified.

As described above, according to the present invention, the fluorescence relaxation time constant of fluorescence which is generated by the fluorochrome is calculated, thereby making it possible to increase the kinds of identifiable fluorochromes. In particular, two kinds of fluorochromes that are different in the fluorescence relaxation time constant are mixed together at a predetermined ratio, thereby making it possible to provide a fluorescence relaxation time constant that is different from two kinds of fluorescence relaxation time constants. As a result, the number of the identifiable fluorochromes are significantly increased. As examples of two kinds of fluorochromes, it is preferable that one kind be a fluorochrome that is selected from a group consisting of Cascade Blue, Cascade Yellow, Alexa Fluor 405, DAPI, Dapoxyl, Dialkylaminocoumarin, Hydroxycoumarin, Marine Blue, Pacific Blue, and PyMPO. Another fluorochrome is preferably a semiconductor quantum fluorochrome that is selected from a group consisting of Q-Dot (product name of Quantum Dot Company) and Evic-Tag (product name of Evident Technology Co.). The former fluorochrome is shorter in the fluorescence relaxation time constant than the latter fluorochrome. The ratio at which those two kinds of fluorochromes are mixed together is changed, thereby making it possible to greatly change the fluorescence relaxation time constant. For example, Q-Dot has the fluorescence relaxation time constant of 20 to 40 nanoseconds.

The fluorescence detecting device according to a first embodiment of the present invention is described above.

Subsequently, a fluorescence detecting device according to a second embodiment of the present invention will be described below.

Figure 9:
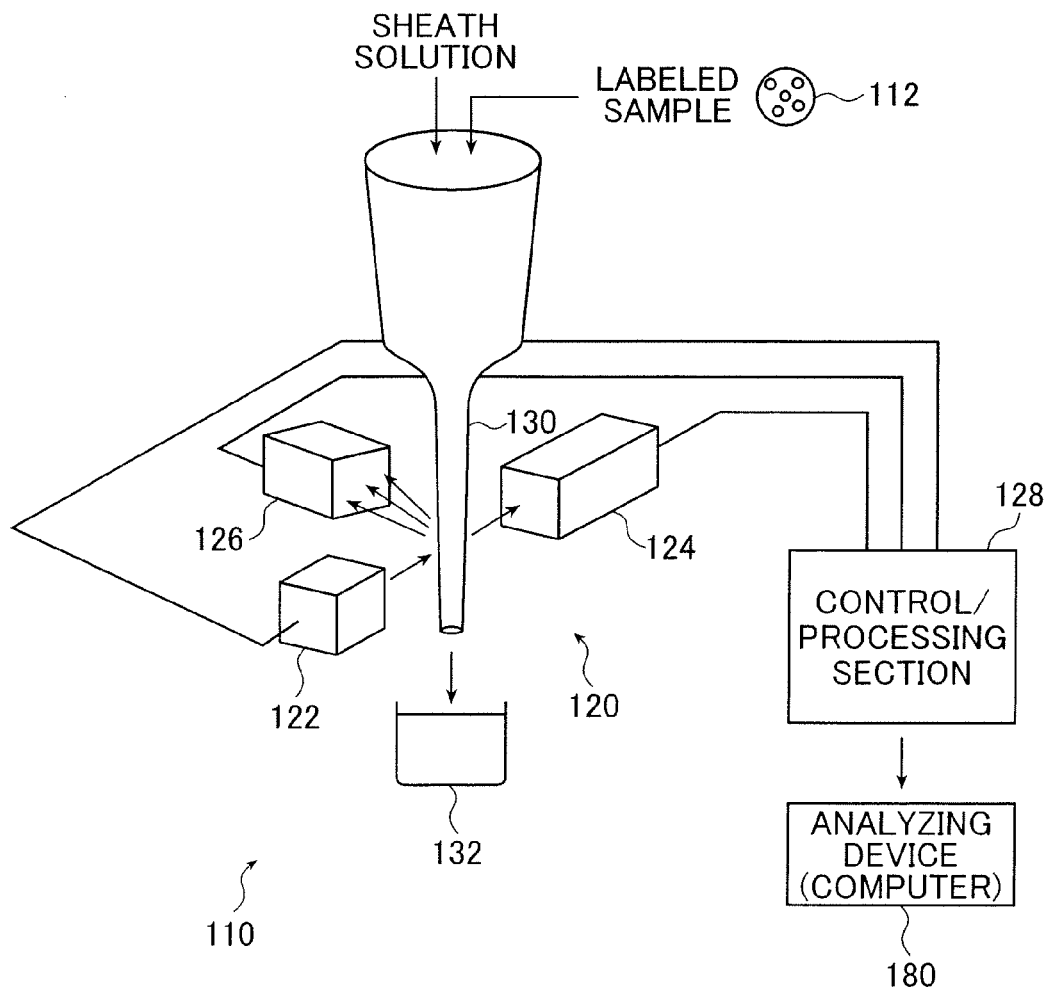
FIG. 9 is a schematic structural diagram showing a flow cytometer using a fluorescence intensity detecting device according to the present invention.

FIG. 9 is a schematic structural diagram showing a flow cytometer 110 using a fluorescence intensity detecting device with an intensity-modulated laser beam according to the present invention.

The flow cytometer 110 includes a signal processing device 120 that irradiates, with a laser beam, labeled samples 112 that are labeled by adhering the fluorochromes to receptor samples (hereinafter referred to as "samples") such as micro beads or specific cells by a chemical coupling or physical coupling, and detects the fluorescence signals of fluorescence that are generated by the labeled samples 112 to process the signals. The flow cytometer 110 also includes an analyzing device (computer) 180 that analyzes the labeled samples 112 according to the processing result which is obtained by the signal processing device 120. The samples themselves conduct autofluorescence according to the irradiation of the laser beam.

The signal processing device 120 includes a laser light source section 122, light receiving sections 124 and 126, a control/processing section 128 having a control section that modulates the laser beam from the laser light source section 122 in intensity at a given frequency and a processing section that processes the fluorescence signals from the labeled samples 112, and a tube 130 that allows the labeled samples 112 to flow together with a sheath solution which forms a high speed flow, thereby forming a flow cell.

An outlet of the duct 130 is equipped with a collecting vessel 132. The flow cytometer 110 may be arranged with a cell sorter for separating and sorting the biologic materials such as specific cells in the labeled samples 112 into different collecting vessels within a short time by using irradiation of the laser beam.

The laser light source section 122 is a section that modulates in intensity the laser beam of continuous wave having a visible band of 350 nm to 800 nm, for example, the laser beam having a wavelength of 405 nm at a given frequency, and outputs the modulated laser beam. The laser light source that outputs the laser beam is formed of, for example, a semiconductor laser, which outputs the laser beam with power of, for example, about 5 to 100 mW. On the other hand, a cycle time of the frequency (modulation frequency) for modulating the intensity of the laser beam is slightly longer than the fluorescence relaxation time (fluorescence relaxation time constant), for example, 10 to 100 MHz.

In the present invention, it is possible to output three laser beams that are different each other in the wavelength, for example, the laser beams of $\lambda_1$=405 nm, $\lambda_2$=533 nm, and $\lambda_3$=650 nm at the same time, as described in the above first embodiment. In this case, it is preferable that three laser beams be bundled into one light beam and irradiated by using the dichotic mirrors as described in the above first embodiment. Further, it is possible to include the signal information on the coding sequences that are orthogonal to each other in each of the laser beams as in the above first embodiment so that which of the laser beams R, G, and B the fluorescence has responded to by the irradiation of the laser beams can be determined.

The laser light source section 122 emits at a predetermined wavelength band so that the laser beam excites the fluorochrome and generates the fluorescence having a specific wavelength band. The fluorescence that is generated by the laser beam includes fluorescence of the autofluorescence that is generated by the labeled samples 112 to be measured per se, and fluorescence that is generated by the fluorochromes on the labeled samples 112. The labeled samples 112 generate the fluorescence at a specific wavelength upon being irradiated with the laser beam at the measurement point when passing by the tube 130.

The light receiving section 124 is so arranged as to face the laser light source section 122 with the tube 130 provided therebetween. The light receiving section 124 includes a photoelectric converter that outputs a detection signal indicating that one of the labeled samples 112 passes by the measurement point, upon receiving the laser beam that has been scattered forward by the labeled sample 112 that passes by the measurement point. The signal that is output from the light receiving section 124 is supplied to the control/processing section 128, and is used as a trigger signal that announces a timing at which the labeled sample 112 passes by the measurement point in the tube 130 in the control/processing section 128.

On the other hand, the light receiving section 126 is disposed orthogonal to an outputting direction of the laser beam that is output from the laser light source section 122, and orthogonal to a moving direction of the labeled sample 12 in the tube 130. The light receiving section 126 includes a photoelectric converter such as a photomultiplier (photoelectron multiple tube) or an avalanche photodiode which receives the fluorescence that is generated by the labeled sample 112 which is irradiated at the measurement point.

Figure 10:
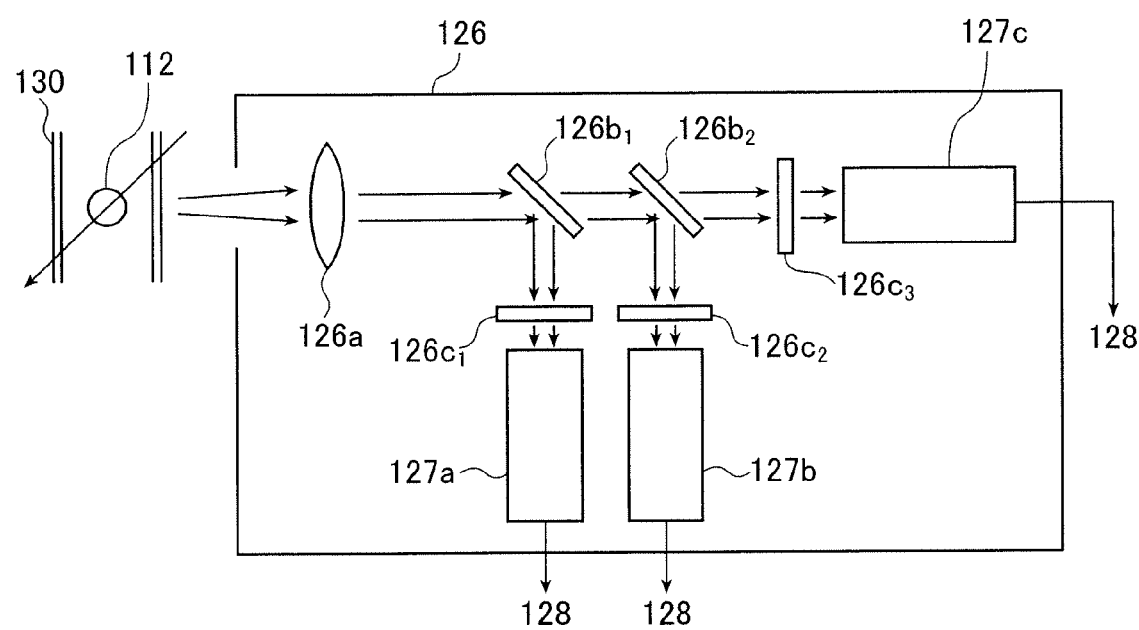
FIG. 10 is a schematic structural diagram showing an example of a light receiving section of the flow cytometer shown in FIG. 1.

FIG. 10 is a schematic structural diagram showing the rough configuration of an example of the light receiving section 126.

The light receiving section 126 shown in FIG. 10 includes a lens system 126a that focuses the fluorescence from the labeled sample 112, dichroic mirrors $126b_1$ and $126b_2$, band pass filters $126c_1$ to $126c_3$, and photoelectric converters 127a to 127c such as the photoelectron multiple tube or the avalanche photodiode.

The lens system 126a is so configured as to focus the fluorescence that has been input to the light receiving section 126 on the light receiving surface of the photoelectric converters 127a to 127c.

The light receiving section 126 has the same configuration as that of the light receiving section 26 of the first embodiment, and has the same perations, and therefore their description will be omitted.

Figure 11:
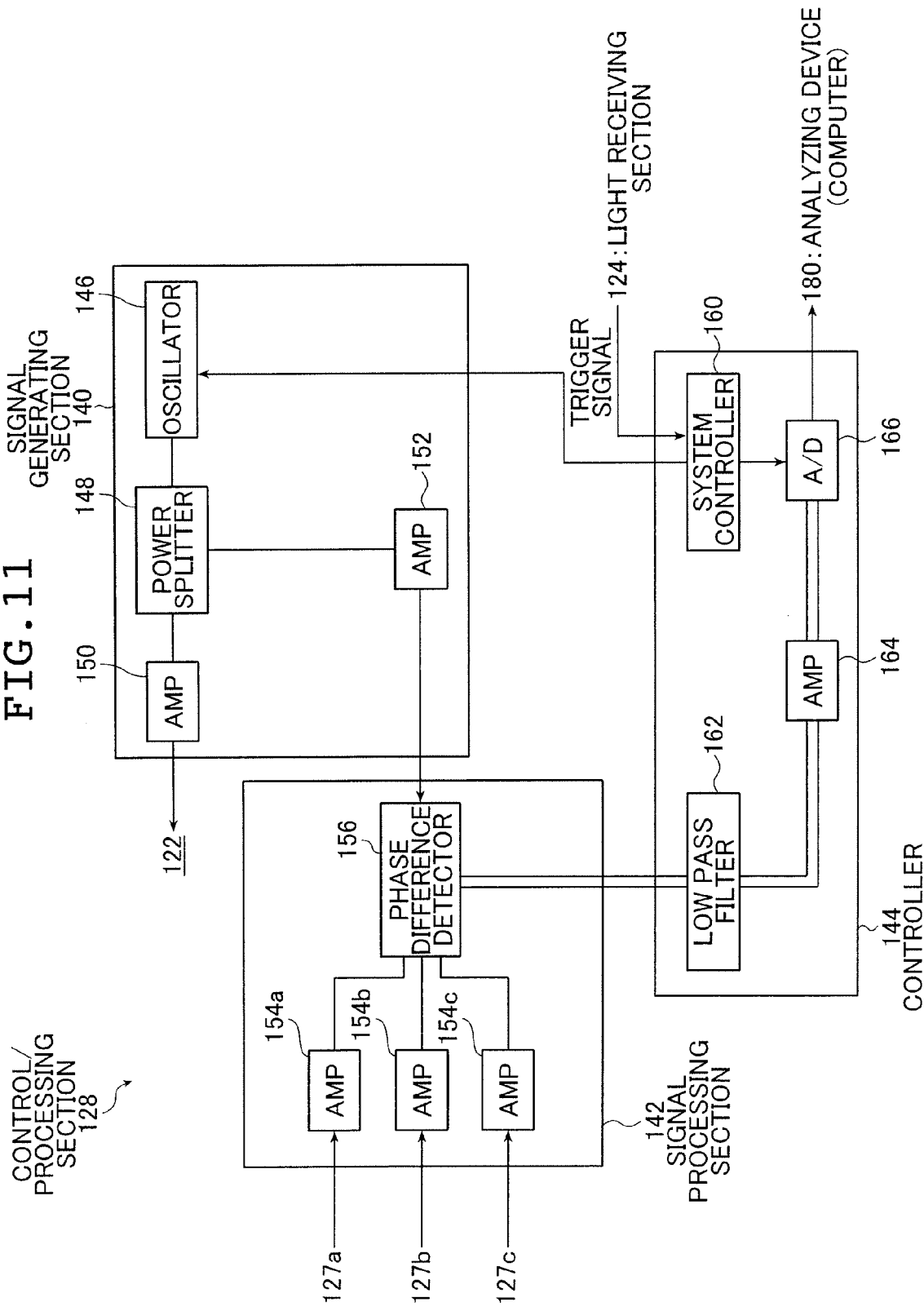
FIG. 11 is a schematic structural diagram showing an example of a control/processing section of the flow cytometer shown in FIG. 1.

As shown in FIG. 11, the control/processing section 128 includes a signal generating section 140, a signal processing section 142, and a controller 144. The signal generating section 140 and the controller 144 form a light source control section that generates a modulation signal having a given frequency.

The signal generating section 140 is a section that generates the modulation signal for modulating (amplitude modulation) the intensity of the laser beam at a given frequency.

More specifically, the signal generating section 140 is a section that has an oscillator 146, a power splitter 148, and amplifiers 150 and 152, and supplies the generated modulation signal to the laser light source section 122 and also to the signal processing section 142. The reason that the modulation signal is supplied to the signal processing section 142 is because the modulation signal is used as a reference signal for detecting the phase difference of the fluorescence signal that is output from the photoelectric converters 127a to 127c as will be described later. The modulation signal is a sine wave signal having a given frequency, and is set to the frequency ranging from 10 to 100 MHz.

The signal processing section 142 has the same configuration as that of the signal processing section 42 in the above first embodiment, and has the same operations, and therefore their description will be omitted. A phase difference detector 156 shown in FIG. 11 is made up of the same power splitter and IQ mixers as the power splitter 56 and the IQ mixers 58*a* to 58*c* shown in FIG. 5.

IQ mixers, which are disposed in the phase difference detector 156 and are not shown, are disposed in the respective photoelectric converters 127*a* to 127*c* so as to mix the fluorescence signals that are supplied from the photoelectric converters 127*a* to 127*c* together with the modulation signal that is supplied from the signal generating section 140 as a reference signal. More specifically, each of the IQ mixers multiplies the reference signal by the fluorescence signal (RF signal) to calculate a processing signal including the cos component (real part) and the high frequency component of the fluorescence signal. The IQ mixer also multiplies a signal that is shifted by 90 degrees with respect to the phase of the reference signal by the fluorescence signal to calculate a processing signal including the sin component (imaginary part) and the high frequency component of the fluorescence signal. The processing signal including the cos component and the processing signal including the sin component are supplied to the controller 144.

The controller 144 is a section that controls the signal generating section 40 so as to generate the sine wave signal having a given frequency as in the controller 44 of the above first embodiment. The controller 144 also removes the high frequency component from the processing signals obtained by the signal processing section 42 and including the cos component and the sin component of the fluorescence signal, thereby obtaining the cos component and the sin component of the fluorescence signal. The controller 144 is different from the controller 44 in that the coding sequence signal for modulating the respective laser beams in pulse is not generated.

The controller 144 gives instructions for controlling the operation of the respective sections. The controller 144 includes a system controller 160 that manages the entire operation of the flow cytometer 110, a low pass filter 162 that removes the high frequency component from the processing signals calculated in the signal processing section 142 which are combinations of the high frequency component and the cos component, the sin component, an amplifier 164 that amplifies the processing signals of the cos component and the sin component from which the high frequency component has been removed, and an A/D converter 166 that samples the amplified processing signals. In the A/D converter 166, the processing signals of the cos component and the sin component from which the high frequency component has been removed are sampled and then supplied to the analyzing device 180.

The analyzing device 180 sets the processing signal value of the cos component (real part) and the sin component (imaginary part) of the fluorescence signal as a vector and causes an inverse matrix that is produced from a predetermined correction conversion matrix to act on the vector to calculate the fluorescence intensity.

Figure 12:
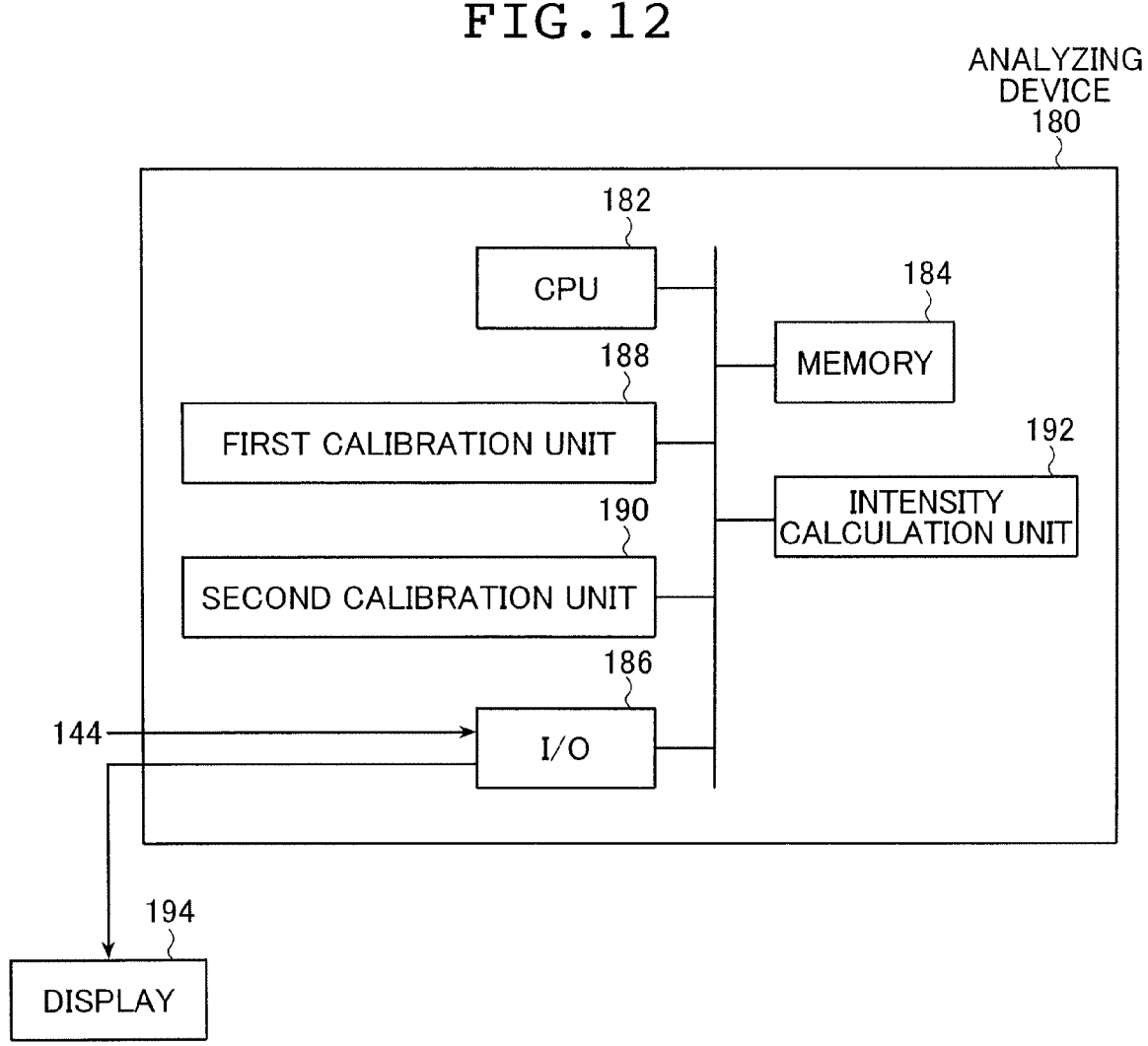
FIG. 12 is a schematic structural diagram showing an example of an analyzing device of the flow cytometer shown in FIG. 1.

FIG. 12 is a schematic structural diagram showing the analyzing device 180.

The analyzing device 180 is a device that is structured by starting given program on the computer. The analyzing device 180 includes a first calibration unit 188 that is formed by executing the software, a second calibration unit 190, and an intensity calculating unit 192 in addition to a CPU 182, a memory 184, and an input/output port 186. Further, the analyzing device 190 is connected with a display 194.

Figure 13:
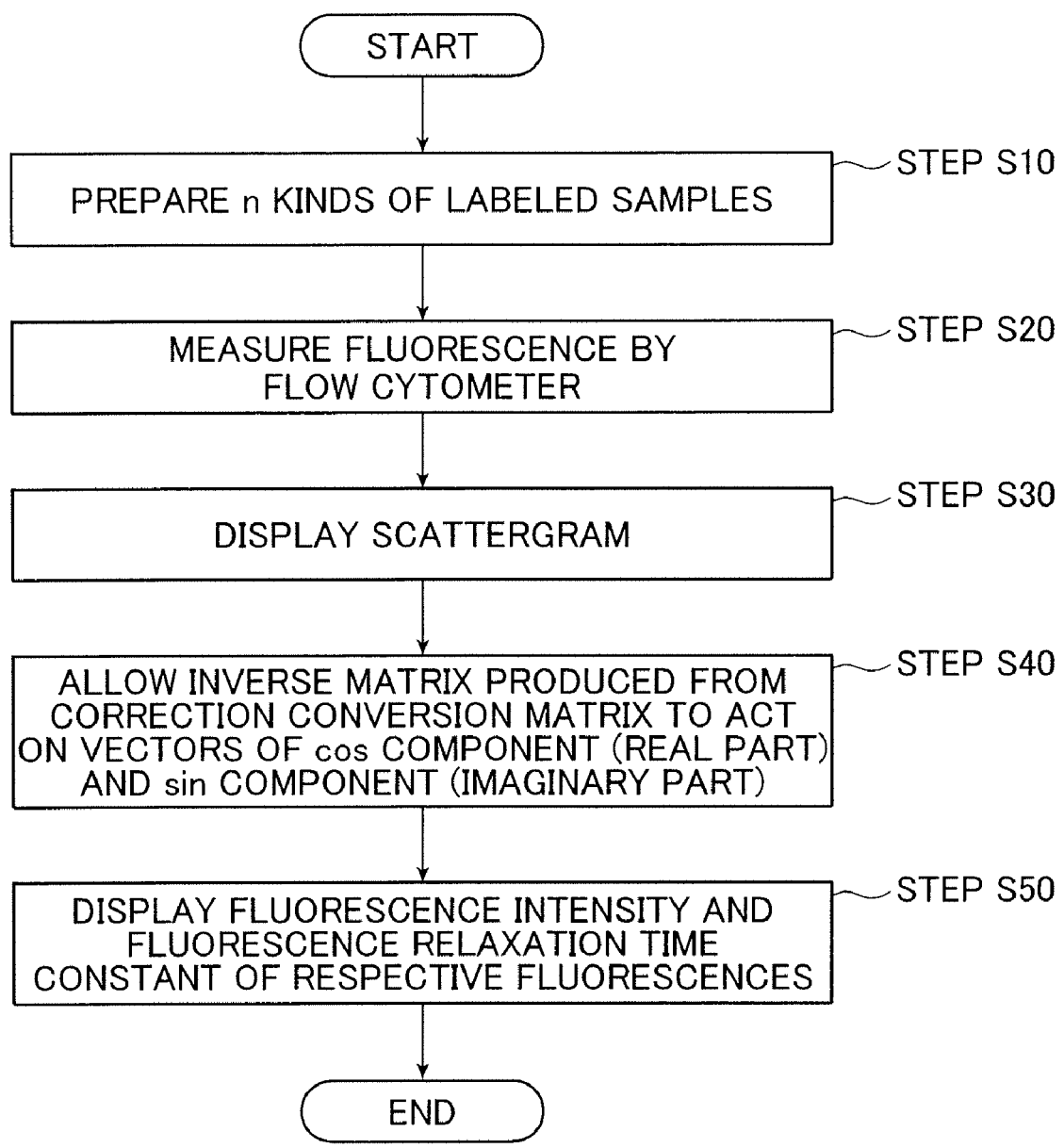
FIG. 13 is a flowchart showing an example of a flow of a fluorescence intensity detecting method according to the present invention.
Figure 14:
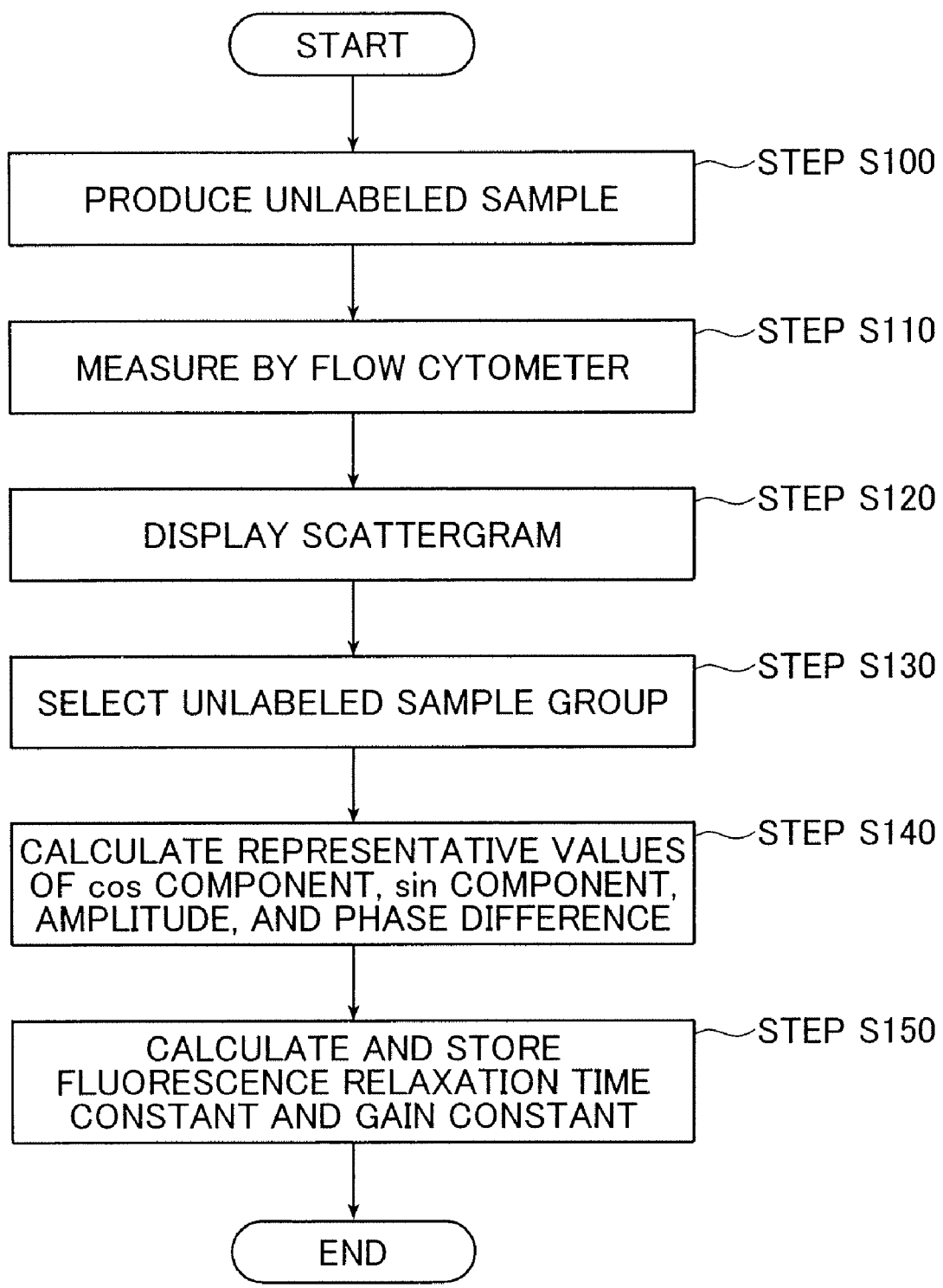
FIG. 14 is a flowchart showing an example of a flow of a first calibration that is conducted in the fluorescence intensity detecting method according to the present invention.
Figure 15:
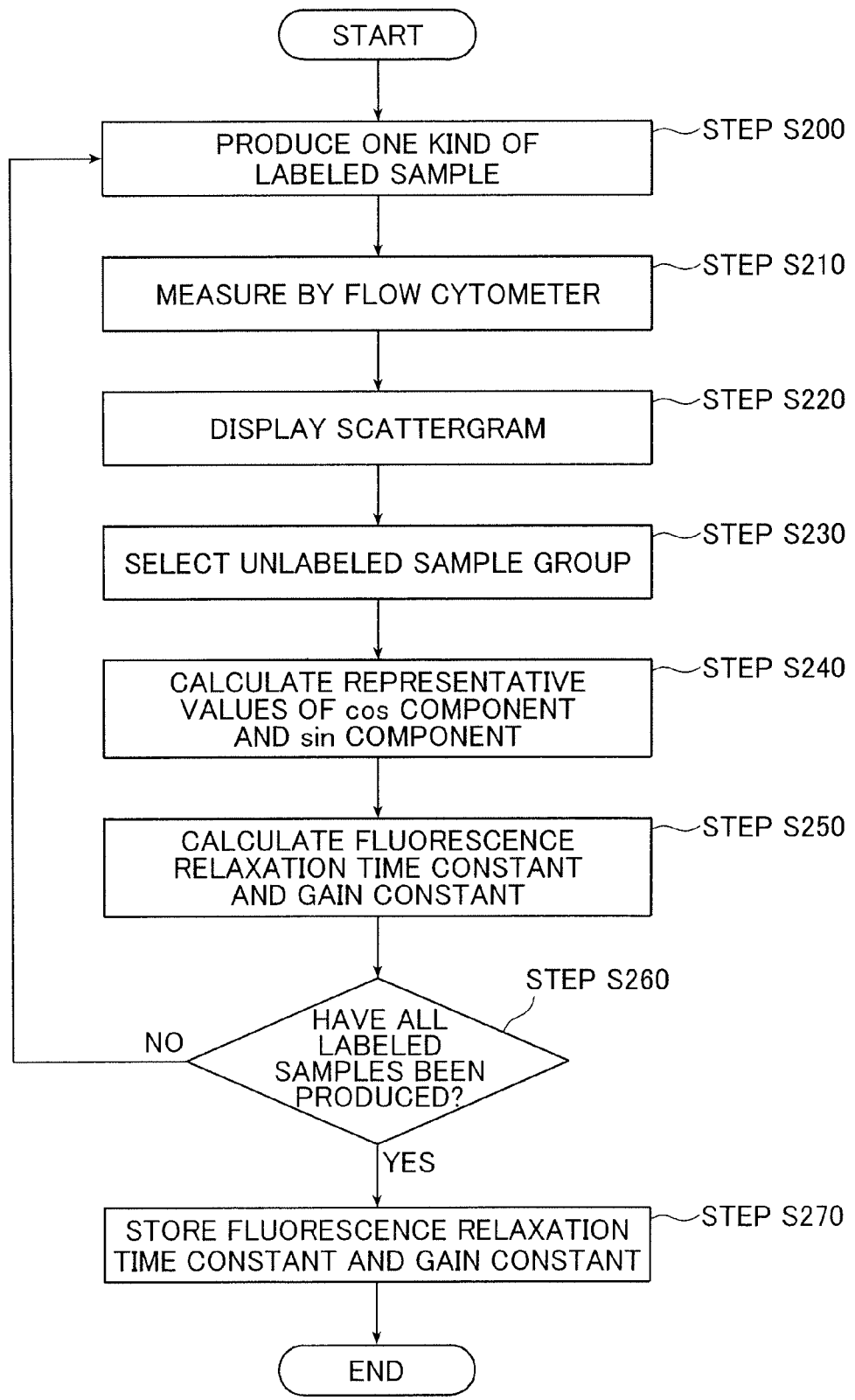
FIG. 15 is a flowchart showing an example of a flow of a second calibration that is conducted in the fluorescence intensity detecting method according to the present invention.

The processing conducted by the analyzing device 180 follows a flow shown in FIGS. 13 to 15. The intensity calculating unit 192 executes a main procedure (Steps S30 to S50) of the processing flow shown in FIG. 13. The first calibration unit 188 executes a main procedure (Steps S120 to S150) of the processing flow shown in FIG. 14. The second calibration unit 190 executes a main procedure (steps S220 to S270) of the processing flow shown in FIG. 15.

The CPU 182 is an calculating processor disposed in the computer, and substantially executes various calculations of the first calibration unit 188, the second calibration unit 190, and the intensity calculation unit 192. The memory 184 includes a ROM that stores program that is executed on the computer to constitute the first calibration unit 188, the second calibration unit 190, and the intensity calculation unit 192 therein, and a RAM that stores the processed results that have been calculated by the first calibration unit 188, the second calibration unit 190, and the intensity calculation unit 192, and data that has been supplied from the input/output port 186 therein.

The input/output port 186 is used to accept input of the detected values of the cos component (real part) and the sin component (imaginary part) of the fluorescence signal that is supplied by the controller 144, and also to output the values of the processed results that have been obtained by the first calibration unit 188, the second calibration unit 190, and the intensity calculation unit 192, or information on the scattergram or the like to the display 194.

The display 194 displays the values of the processed results such as the fluorescence relaxation time constant or the gain constant which has been obtained by the first calibration unit 188, the second calibration unit 190, and the intensity calculation unit 192, or a graph of the scattergram.

The intensity calculation unit 192 is a portion that executes the main portion of the processing flow shown in FIG. 13, and obtains the respective fluorescence intensities from the detected values of the cos component and the sin component which have been supplied by the controller 144. In other words, the intensity calculation unit 192 sets the matrix elements of the correction conversion matrix by using the parameters (gain constant, fluorescence relaxation time constant) of a transfer function when all of the fluorescence of the labeled samples that have been irradiated with the laser beam are relaxation responses of first order lag systems, and obtains the matrix elements of the correction conversion matrix, to thereby produce a correction conversion matrix. Then, the intensity calculation unit 192 sets pairs of detected values of the cos components and the sin components (detected value including the phase information) as vectors, the pairs of detected values acquired from the respective detection sensors which are supplied from the controller 144. Then, the intensity calculation unit 192 allows the inverse matrix that has been produced from the correction conversion matrix produced in advance to act on the vectors, to thereby calculate the fluorescence intensity of the fluorescence that is generated by the labeled samples. The details of the processing of the intensity calculation unit 192 will be described later.

The labeled samples 112 are labeled by adhering different kinds of fluorochromes to the samples such as the cells or the micro beads. In this case, when the number of kinds of labeled samples is n and the number of photoelectric detectors is m, m and n are so set as to meet $2 \cdot m \geq n+1$.

The first calibration unit 188 is a portion that obtains the fluorescence relaxation time constant and the gain constant when the autofluorescence that is generated by an unlabeled sample is the relaxation response of the first order lag system. A sample that has no fluorochrome adhered thereon and generates by itself the autofluorescence such as a micro bead is called "unlabeled sample". More specifically, the first calibration unit 188 irradiates the unlabeled sample as an object to be measured with the time modulated laser beam at a given frequency to acquire the detected values including the phase information from the respective photoelectric converters, calculates the fluorescence relaxation time constant and the gain constant of the autofluorescence that is generated by the unlabeled sample, and stores those values in the memory 184. The details will be described later.

The second calibration unit 190 is a portion that calculates the fluorescence relaxation time constant and the gain constant of the fluorescence in all kinds of the labeled samples having kinds of fluorochromes, individually. Likewise, in this case, it is assumed that the fluorescence that is generated by each kind of fluorochrome is a relaxation response of a first order lag system.

That is, the second calibration unit 190 prepares the labeled samples with only one kind of fluorochrome (samples such as the micro beads that are adhered to one kind of fluorochrome and generates the autofluorescence), and irradiates the labeled sample as an object to be measured with the time modulated laser beam at a given frequency, to thereby acquire the detected values including the phase information from the respective detection sensors, and calculates a fluorescence relaxation time constant and a gain constant of the fluorescence that is generated by the labeled sample based on those detected values. Then, the second calibration unit 190 calculates the fluorescence relaxation time constants and the gain constants of all the fluorescence that is generated by the fluorochromes of the labeled samples while sequentially changing kinds of fluorochromes included in the labeled samples. The second calibration unit 190 then stores the calculated fluorescence relaxation time constants and gain constants in the memory 184. The detailed description will be described later.

As described above, the fluorescence relaxation time constants and the gain constants of the autofluorescence and the fluorescence that is generated by the fluorochrome, which are calculated by the first calibration unit 188 and the second calibration unit 190 and stored in the memory 184, are employed as the parameters of the transfer function and employed for calculation of the matrix elements of the correction conversion matrix when the correction conversion matrix is produced in the intensity calculation unit 192. The reason that the fluorescence relaxation time constant and the gain constant of the autofluorescence which are calculated by the first calibration unit 188 are employed is because a precision in the results of calculating n fluorescence intensities that are generated by the fluorochromes is prevented from being deteriorated by the autofluorescence that is generated from the labeled samples.

Further, the reason that the fluorescence relaxation time constants and the gain constants of the fluorescence which are calculated by the second calibration unit 190 are employed in calculation of the matrix elements of the above correction conversion matrix is because the fluorescence intensities can be obtained with high precision when fluorescence that is generated from the n fluorochromes are measured at the same time. In other words, the intensity calculation unit 192 produces the correction conversion matrix by using the fluorescence relaxation time constant and the gain constant of the autofluorescence which have been stored in the memory 184 and known, and the fluorescence relaxation time constants and the gain constants of the respective fluorochromes which have been stored in the memory 184 and known, and obtains the fluorescence intensities by using the correction conversion matrix. The detailed description will be described later.

The analyzing device 180 is structured as described above.

The flow cytometer 110 configured as described above conducts the processing shown in FIG. 13, and obtains the fluorescence intensities of the respective fluorescence.

First, the flow cytometer 110 prepares n kinds of labeled samples (Step S10). The n kinds of labeled samples are labeled by adhering n kinds of fluorochromes to the samples such as the micro beads, and mixed in the measurement solution. The solution of the labeled sample forms a flow cell within the tube 130 by using the sheath solution. The flow cytometer 110 irradiates the flow cell with an intensity-modulated laser beam at a given frequency to measure the fluorescence (Step S20).

In the measurement of the fluorescence, the flow cytometer 110 starts the measurement by means of m photoelectric converters that are different in the wavelength band (m=3 in the embodiment shown in FIG. 10) in response to a trigger signal that is generated by the light receiving section 124 which announces a timing at which one of the labeled samples 112 passes by the measurement point of the tube 130.

The processing signal including the cos component and the sin component of the fluorescence signal are extracted from the fluorescence signal obtained by measurement in the phase difference detector 156 of the signal processing section 142. A high frequency signal is removed from the processing signals by means of the low pass filter 162 in the controller 144, and the cos component and the sin component of the fluorescence signals are subjected to A/D conversion and obtained as the detected values in the controller 144.

The cos component and the sin component thus obtained are supplied to the analyzing device 180, and the scattergram (two-dimensional correlation diagram) is displayed on the display 194 by using the cos component and the sin component which have been obtained within a given measurement time (Step S30).

The scattergram is displayed on the display 194, and the detected values of the cos component and the sin component which have been detected in each of the photoelectric converters are dealt with as the vector components, and the inverse matrix that is produced from the correction conversion matrix which will be described later is allowed to act on the vector (Step S50). When the inverse matrix acts on the vector, the gain constants in the fluorescence which is generated by the respective labeled samples are obtained. The gain constants are obtained as the vector of the ratios of the fluorescence intensities.

The ratios of the fluorescence intensities thus obtained and the fluorescence relaxation time constant are displayed on the display 194 (Step S50).

In the example, the matrix elements of the correction conversion matrix are produced as follows.

When it is assumed that the fluorescence that is generated by the labeled samples are in a relaxation process of first order lag system, the detected values (cos component, sin component) that are output from the respective photoelectric converters are represented as the following formulae (12) and (13) by adding the transfer functions of the respective first order lag systems of the fluorescence from the n kinds of fluorochromes and one kind of autofluorescence.

[EX. 12]

$$(\cos \text{component})_j = \frac{\kappa_{1j} \cdot \tau_1 \cdot \alpha_1}{1 + (\tau_1 \cdot \omega_M)^2} + \frac{\kappa_{2j} \cdot \tau_2 \cdot \alpha_2}{1 + (\tau_2 \cdot \omega_M)^2} \cdots + \frac{\kappa_{nj} \cdot \tau_n \cdot \alpha_n}{1 + (\tau_n \cdot \omega_M)^2} + \frac{\kappa_{0j} \cdot \tau_0 \cdot \alpha_0}{1 + (\tau_0 \cdot \omega_M)^2} \quad (12)$$

-continued

[EX. 13]

$$(\text{sin component})_j = -\frac{\kappa_{1j} \cdot \tau_1 \cdot \omega_M(\tau_1 \cdot \alpha_1)}{1+(\tau_1 \cdot \omega_M)^2} - \frac{\kappa_{2j} \cdot \tau_2 \cdot \omega_M(\tau_2 \cdot \alpha_2)}{1+(\tau_1 \cdot \omega_M)^2} \cdots \frac{\kappa_{nj} \cdot \tau_n \cdot \omega_M(\tau_n \cdot \alpha_n)}{1+(\tau_1 \cdot \omega_M)^2} - \frac{\kappa_{0j} \cdot \tau_0 \cdot \omega_M(\tau_0 \cdot \alpha_0)}{1+(\tau_1 \cdot \omega_M)^2} \quad (13)$$

In the above formulae, $\tau_i$ (i=1 to n) is a fluorescence relaxation time constant of the fluorescence that is generated by an i-th kind of fluorochrome. Further, $\kappa_{ij}$ (i=1 to n, j=1 to m) is a gain constant when the fluorescence that is generated by the i-th kind of fluorochrome is detected by a j-th photoelectric converter, and normalized by the maximum gain constant among the gain constants that are detected by m photoelectric converters.

Further, $\tau_0$ is a fluorescence relaxation time constant when the labeled sample generates the autofluorescence. Further, $\kappa_{0j}$ (j=1 to m) is a gain constant when the autofluorescence is generated by the labeled sample is detected by the j-th photoelectric converter, and normalized by the maximum gain constant among the gain constants that are detected by the m photoelectric converters.

Those values are calculated by the first calibration (processing shown in FIG. 14) and the second calibration (processing shown in FIG. 15) which will be described later, and stored in the memory 184. The $\omega_M$ is an angular frequency obtained by multiplying the modulation frequency of the laser beam by $2\pi$.

On the other hand, $\alpha_i$ (i=1 to n) is a gain constant of the fluorescence that is generated by the fluorochrome when the fluorescence of the n kinds of fluorochromes and one kind of autofluorescence are generated at the same time, and the gain constant represents the fluorescence intensity when the laser beams are irradiated at the same time. The $\alpha_0$ is a gain constant of the autofluorescence when the fluorescence of the n kinds of fluorochromes and one kind of autofluorescence are generated at the same time. Those gain constants $\alpha_i$ and $\alpha_0$ are unknown values representative of the fluorescence intensities and to be calculated when the labeled samples that are labeled by n kinds of fluorochromes are irradiated with the laser beam at the same time.

Accordingly, an equation is represented by the following formula (14) by using the correction conversion matrix M from the formulae (12) and (13) as represented. In this example, as a matrix element of the correction conversion matrix M, for example, the matrix element in the first row, first column is $\kappa_{11}/(1+(\tau_1 \cdot \omega_M)^2)$.

The correction conversion matrix M in which the value of the transfer function is a matrix element is produced as described above.

The matrix size of the correction conversion matrix M is $2 \cdot m \times (n+1)$ (longitudinal direction×lateral direction). In this expression, m and n is so set as to meet $2 \cdot m \geq n+1$ as described above. Therefore, the size of the correction conversion matrix in the longitudinal direction is reduced, and for example, a line having a smaller value of $\theta_{ij}$ is removed to provide a matrix size of $(n+1)\times(n+1)$. As a result, the matrix of the correction conversion matrix M is reduced in size, the inverse matrix $M'^{-1}$ of the reduced square matrix M' is obtained and the right side vector X in the formula (14) is calculated by the inverse matrix $M'^{-1}$ acting on the left side vector A of the formula (14) (Step S40).

[EX. 14]

$$\begin{Bmatrix} (\text{cos component})_1 \\ (\text{sin component})_1 \\ (\text{cos component})_2 \\ (\text{sin component})_2 \\ \vdots \\ \vdots \\ \vdots \\ (\text{cos component})_m \\ (\text{sin component})_m \end{Bmatrix}_A = [M] \begin{Bmatrix} \tau_1 \cdot \alpha_1 \\ \tau_2 \cdot \alpha_2 \\ \vdots \\ \vdots \\ \vdots \\ \vdots \\ \vdots \\ \tau_n \cdot \alpha_n \\ \tau_0 \cdot \alpha_0 \end{Bmatrix}_X \quad (14)$$

Apart from the method of reducing the matrix size as described above, it is possible that both sides of the expression (14) are multiplied by a transposed matrix $M^t$ of the correction conversion matrix M, the correction conversion matrix is converted into the square matrix $M^t \cdot M$ having the matrix size of $(n+1)\times(n+1)$, the inverse matrix $(M^t \cdot M)^{-1}$ of the square matrix is allowed to act on $M^t A$, thereby calculating the vector X $(=(M^t \cdot M)^{-1} \cdot M^t A)$ of the right side of the formula (14), in which the $M^t A$ is obtained by multiplying the vector A of the left side of the formula (14) by the transposed matrix.

Since $\tau_i$ (i=1 to n) whose value is known is included in the vector X on the right side of the formula (14) obtained as described above, those values are substituted for the $\tau_i$, and $\alpha_i$ (i=1 to n) and $\alpha_0$ are calculated from the calculated vector X.

Finally, the fluorescence relaxation time constants $\tau_i$, $\tau_0$ and the gain constants $\alpha_i$, $\alpha_0$ of the respective fluorescence are displayed on the display 94. The gain constants $\alpha_i$ and $\alpha_0$ represent the fluorescence intensities of the respective fluorescence.

As described above, $\tau_0$ and $\kappa_{0j}$ that are stored in the memory 184 are employed in producing the correction conversion matrix M, and those values are calculated by the first calibration shown in FIG. 14.

The first calibration will be described below.

In the first calibration shown in FIG. 14, the unlabeled sample is first prepared (Step S100).

The unlabeled sample is one kind of sample in the solution and generates autofluorescence by irradiation of the laser beam. As the above sample, a receptor sample such as a micro bead or a cell having whisker that can be coupled with antibody is exemplified.

Then, the unlabeled sample is measured by the flow cytometer (Step S110).

The measurement (Step S110) using the flow cytometer and the display (Step S120) of the scattergram are the same operations as those in Steps S20 and S30 shown in FIG. 13, and their description is omitted.

Subsequently, in order to specify the autofluorescence that is generated by the unlabeled sample, a sample group of the fluorescence region of the unlabeled sample is selected in the scattergram displayed on the display 194 (Step S130). The selection is done with the input operation system such as a mouse used by an operator. The cos component and the sin component of the unlabeled sample included in the region of the selected sample group, or the representative values (for example, an average value, a gravity center value, a frequency peak value) of the amplitude and the phase difference of the fluorescence signal are obtained (Step S140).

Subsequently, the fluorescence relaxation time constant and the gain constant are obtained by the following formulae (15) to (18) that define the relationship between the representative values and the fluorescence relaxation time constant as well as the gain constant by using the obtained representative values (Step S150).

[EX. 15]
$$(\text{amplitude})_j = C \cdot \frac{\tau_0 \cdot \alpha_{0j}}{\sqrt{1 + (\tau_0 \cdot \omega_M)^2}} \quad (15)$$

[EX. 16]
$$(\theta)_j = -\tan^{-1}(\tau_0 \cdot \omega_M) \quad (16)$$

[EX. 17]
$$(\cos\text{ component})_j = C \cdot \frac{\tau_0 \cdot \alpha_{0j}}{1 + (\tau_0 \cdot \omega_M)^2} \quad (17)$$

[EX. 18]
$$(\sin\text{ component})_j = -C \cdot \frac{\tau_0^2 \cdot \alpha_{0j} \cdot \omega_M}{1 + (\tau_0 \cdot \omega_M)^2} \quad (18)$$

In these formulae, $\tau_0$ is the fluorescence relaxation time constant of the autofluorescence of the sample that generates the autofluorescence, and $\omega_M$ is an angular frequency obtained by multiplying the modulation frequency of the laser beam by $2\pi$. $\alpha_{0j}$ is the gain constant of the autofluorescence that is obtained by the j-th (j=1 to m) photoelectric converter. C is a proportional constant. The fluorescence relaxation time constant $\tau_0$ of the autofluorescence and the gain constant $\alpha_{0j}$ of the autofluorescence are calculated by using any two of the formulae (15) to (18).

The fluorescence relaxation time constant and the gain constant of the unlabeled sample which are thus calculated are stored in the memory 184 (Step S150).

The first calibration is conducted as described above.

Subsequently, the second calibration will be described.

In the second calibration shown in FIG. 15, a labeled sample to which one kind of fluorochrome is adhered is prepared among n kinds of labeled samples (Step S200). Here, a kind of a labeled sample means a sample to which one kind of fluorochrome is adhered and generates the autofluorescence such as a micro bead.

Then, the fluorescence is measured by means of the flow cytometer 110 (Step S210), and the measured result is displayed on the scattergram (Step S220). A sample group of one kind of the labeled sample is selected from the scattergram.

The measurement that is conducted by the flow cytometer (Step S210) and the display of the scattergram (Step S220) are the same operations as those in Steps S20 and S30 shown in FIG. 13, and their description is omitted.

The selection of the sample group is done in order to specify the autofluorescence that is generated by the sample in one kind of labeled sample. More specifically, in the scattergram that is displayed on the display 94, the sample group of the fluorescence region of one kind of labeled sample is selected. The selection is done with an input operation system such as a mouse used by an operator, to thereby obtain the cos component and the sin component of the fluorescence that are generated by the labeled samples included in the region of the selected sample group, or the representative values (for example, the average value, the gravity center value, the frequency peak value) of the amplitude and the phase difference of the fluorescence signal (Step S240).

Subsequently, the fluorescence relaxation time constant and the gain constant of the fluorescence that is generated by the fluorochrome of the labeled sample are calculated from the following formulae (19) to (21) by using the representative values obtained above and the fluorescence relaxation time constant and the gain constant of the autofluorescence that is generated by the labeled sample which are calculated in the first calibration and stored in the memory 184 (Step S250).

[EX. 19]
$$\tau_i = \frac{1}{\omega_M} \cdot \frac{(\sin\text{ component})_{[2]} - \frac{\kappa_{0[2]}}{\kappa_{0[1]}} \cdot (\sin\text{ component})_{[1]}}{\frac{\kappa_{0[2]}}{\kappa_{0[1]}} \cdot (\cos\text{ component})_{[1]} - (\cos\text{ component})_{[2]}} \quad (19)$$

[EX. 20]
$$\alpha_{0\max} = \frac{\left\{\begin{array}{c}\tau_i \cdot \omega_M \cdot (\cos\text{ component})_{[1]} + \\ (\sin\text{ component})_{[2]}\end{array}\right\}}{(\tau_i - \tau_0) \cdot \omega_M \cdot \kappa_{0[1]} \cdot \tau_0} \cdot \{1 + (\tau_0 \cdot \omega_M)^2\} \quad (20)$$

[EX. 21]
$$(\cos\text{ component})_{[1]} = \frac{\tau_i \cdot \alpha_{i[1]}}{1 + (\tau_i \cdot \omega_M)^2} + \frac{\kappa_{0[1]} \cdot \tau_0 \cdot \alpha_{0\max}}{1 + (\tau_0 \cdot \omega_M)^2} \quad (21)$$

Here, the subscripts [1] and [2] in the expression (19) are the number of the photoelectric converter whose amplitude value is the maximum and the number of the photoelectric converter whose amplitude value is the second largest, among the amplitudes $((\cos\text{ component})^2+(\sin\text{ component})^2))^{1/2}$ of the fluorescence signal that is obtained by the plural photoelectric converters. Therefore, $\kappa_{0[1]}$ and $\kappa_{0[2]}$ are ratios that are normalized by the maximum gain of the gain constant that has been calculated in the first calibration, and have known values since numbers of the subscripts [1] and [2] are already known.

The fluorescence relaxation time constant $\tau_i$ that has been calculated by the formula (19) is stored in the memory 184 in order that the fluorescence relaxation time constant $\tau_i$ is employed to calculate the values of the matrix elements of the correction conversion matrix in the expression (14) in the processing flow shown in FIG. 13. Further, $\alpha_{0max}$ is calculated from the formula (20) by using the fluorescence relaxation time constant $\tau_j$. The $\alpha_{0max}$ is the maximum gain constant of the autofluorescence in the second calibration. The $\alpha_{0max}$ is substituted for the formula (21), thereby making it possible to calculate $\alpha_{i[1]}$. The $\alpha_{i[1]}$ is the gain constant of the fluorescence that has been received by the numbered photoelectric converter whose amplitude value is the maximum among the fluorescence that is generated by the fluorochrome.

Likewise, the gain constant $\alpha_{ij}$ of the fluorescence that has been received by the j-th photoelectric converter in the formula (22) is calculated by using the following formula (22).

[EX. 22]
$$(\cos\text{ component})_j = \frac{\tau_i \cdot \alpha_{ij}}{1 + (\tau_i \cdot \omega_M)^2} + \frac{\kappa_{0j} \cdot \tau_0 \cdot \alpha_{0\max}}{1 + (\tau_0 \cdot \omega_M)^2} \quad (22)$$

The fluorescence relaxation time constants and the gain constants which have been thus calculated are stored in the memory 184. The calculated values are parameters of the fluorescence in one kind of a labeled sample. Accordingly, it is determined whether n kinds of labeled samples are prepared, respectively, to obtain the parameters of the fluorescence, or not (Step S260).

As a result of the determination, in the case where all kinds of labeled samples are not prepared, and the parameters of the fluorescence of the labeled samples are not calculated, the processing is returned to Step S200, and Steps S200 to S250 are repeated.

In this way, the fluorescence relaxation time constant and the gain constant in each of the fluorochromes are calculated according to the measurement of the fluorescence in each kind of the labeled samples, and stored in the memory 184.

The fluorescence relaxation time constants and the gain constants which have been stored in the memory 184 in this way are employed to prepare the correction conversion matrix in the step S40 shown in FIG. 13 which is being processed.

The above description has been given of the second calibration.

The gain constant $\alpha ij$ (i=1 to n, j=1 to m) which has been calculated in the second calibration is normalized by the gain constant max($\alpha ij$) that is the maximum among those gain constants when i is fixed and j is changed, thereby making it possible to obtain $\kappa ij$ that is used in the correction conversion matrix in the formula (14). In addition, the normalized $\kappa ij$ is stored in the memory 184 in order that the normalized $\kappa ij$ is used to calculate the value of the matrix element of the correction conversion matrix in the expression (22) in the processing flow shown in FIG. 13.

As described above, according to the present invention, even if n kinds of labeled samples are irradiated with the laser beam, it is possible to obtain the gain constant corresponding to the fluorescence intensity on the basis of the processing flow shown in FIG. 13. In this situation, since the laser beam is modulated in time at the given frequency, it is possible to obtain the values of the cos component and the sin component from one photoelectric converter. Accordingly, since the fluorescence intensity is obtained by using those values, the number of labeled samples which can be obtained by the measurement is not limited to the number equal to or less than the number of disposed photoelectric converters, which is different from the conventional art. In other words, in the case where the number of disposed photoelectric converters is fixed, it is possible to increase the kinds of identifiable fluorescence as compared to those in the conventional art.

Further, since the first calibration and the second calibration for calculating the fluorescence relaxation time constants and the gain constants by using the unlabeled sample and each kind of labeled samples are conducted before conducting the processing shown in FIG. 13 on n kinds of labeled samples, it is possible to obtain the fluorescence intensity with high precision in conducting the processing shown in FIG. 13.

The invention claimed is:

1. A fluorescence detecting device using an intensity-modulated laser beam, which irradiates an object to be measured with a laser beam to receive fluorescence generated by the object to be measured, and carries out signal processing of a fluorescence signal obtained when receiving the fluorescence, comprising:
    a laser light source section that outputs the laser beam with which the object to be measured is irradiated;
    a light receiving section that outputs the fluorescence signal of the fluorescence generated by the object to be measured which is irradiated with the laser beam;
    a light source control section that generates a modulation signal having a given frequency in order to time-modulate an intensity of the laser beam that is output from the laser light source section; and
    a processing section that calculates, by using the modulation signal, a fluorescence relaxation time of the fluorescence of the object to be measured based on the fluorescence signal that is output from the light receiving section by irradiating the object to be measured with the time-modulated laser beam,
    wherein the processing section obtains a phase delay with respect to the modulation signal of the fluorescence signal to calculate the fluorescence relaxation time,
    wherein the light source control section uses as a pulse control signal a coding sequence signal that is selected from a plurality of coding sequence signals which have signal values of one bit coded with a given length and are orthogonal to each other, and sets and controls on/off of output of the laser beam so that an on-time of the output of the laser beam from the laser light source section is longer than one cycle time of the time modulation of the laser beam, and
    wherein the processing section calculates the fluorescence relaxation time and identifies the fluorescence from the object to be measured, by using the coding sequence signal based on a light receiving signal that is output from the light receiving section.

2. A fluorescence detecting device using an intensity-modulated laser beam, which irradiates an object to be measured with a laser beam to receive fluorescence generated by the object to be measured, and carries out signal processing of a fluorescence signal obtained when receiving the fluorescence, comprising:
    a laser light source section that outputs the laser beam with which the object to be measured is irradiated;
    a light receiving section that outputs the fluorescence signal of the fluorescence generated by the object to be measured which is irradiated with the laser beam;
    a light source control section that generates a modulation signal having a given frequency in order to time-modulate an intensity of the laser beam that is output from the laser light source section; and
    a processing section that calculates, by using the modulation signal, a fluorescence relaxation time of the fluorescence of the object to be measured based on the fluorescence signal that is output from the light receiving section by irradiating the object to be measured with the time-modulated laser beam,
    wherein the light source control section uses as a pulse control signal a coding sequence signal that is selected from a plurality of coding sequence signals which have signal values of one bit coded with a given length and are orthogonal to each other, and sets and controls on/off of output of the laser beam so that an on-time of the output of the laser beam from the laser light source section is longer than one cycle time of the time modulation of the laser beam, and
    wherein the processing section calculates the fluorescence relaxation time and identifies the fluorescence from the object to be measured, by using the coding sequence signal based on a light receiving signal that is output from the light receiving section.

3. The fluorescence detecting device using an intensity-modulated laser beam according to claim 2, wherein the plurality of coding sequence signals are configured by shifting one coding sequence signal in a bit direction and the coding sequence signals become orthogonal to each other by the shifting.

4. The fluorescence detecting device using an intensity-modulated laser beam according to claim 2,
   wherein the laser light source section includes a plurality of laser light sources that output a plurality of laser beams,
   wherein the light source control section controls the on/off of outputs of the laser beams from the plurality of laser light sources by using the plurality of coding sequence signals that are orthogonal to each other, and
   wherein the processing section separates each of fluorescence signals of the fluorescence that is generated by the object to be measured by irradiation of the respective laser beams, from the fluorescence signals which are overlapped together and outputted from the light receiving section, including optical signals of the plurality of laser beams, by using the coding sequence signals used for the outputs of the laser beams.

5. A fluorescence detecting device using an intensity-modulated laser beam, which irradiates an object to be measured with a laser beam to receive fluorescence generated by the object to be measured, and carries out signal processing of a fluorescence signal obtained when receiving the fluorescence, comprising:
   a laser light source section that outputs the laser beam with which the object to be measured is irradiated;
   a light receiving section that outputs the fluorescence signal of the fluorescence generated by the object to be measured which is irradiated with the laser beam;
   a light source control section that generates a modulation signal having a given frequency in order to time-modulate an intensity of the laser beam that is output from the laser light source section; and
   a processing section that calculates, by using the modulation signal, a fluorescence relaxation time of the fluorescence of the object to be measured based on the fluorescence signal that is output from the light receiving section by irradiating the object to be measured with the time-modulated laser beam,
   wherein the object to be measured includes a plurality of labeled samples that are labeled by a plurality of fluorochromes that generate different kinds of fluorescence,
   wherein the light receiving section includes an input section that acquires, by receiving fluorescence of the labeled samples generated by irradiation of the laser beam by a plurality of detection sensors that are different in light receiving wavelength band, detected values of the fluorescence signal including phase information from each of the respective detection sensors, and
   wherein the processing section includes:
      a matrix producing section that calculates fluorescence relaxation times of the fluorescence that is generated by the fluorochromes, and sets matrix elements of a correction conversion matrix for obtaining fluorescence intensities by using the calculated fluorescence relaxation times, to thereby produce the correction conversion matrix; and
      an intensity calculating section that obtains, with a set of the detected values of the fluorescence signals including the phase information acquired from the respective detection sensors as a vector, the fluorescence intensities of the fluorescence that is generated by the respective labeled samples by allowing an inverse matrix produced from the correction conversion matrix to act on the vector.

6. The fluorescence detecting device according to claim 5,
   wherein the labeled samples include a plurality of different kinds of samples by adhering the fluorochromes that are different in kind from each other to samples that generate autofluorescence by irradiation of the laser beam, and
   wherein the fluorescence that is generated from at least one kind of fluorochrome among the fluorochromes and the autofluorescence that is generated from the samples by irradiation of the labeled samples with the laser beam have wavelength spectrums partially overlapped each other in a wavelength region.

7. The fluorescence detecting device according to claim 6,
   wherein the processing section includes a first calibration section that obtains the fluorescence relaxation time and a gain constant when it is assumed that the autofluorescence is a relaxation response of a first order lag system in an unlabeled sample, where a sample to which any fluorochrome are not adhered and which generates the autofluorescence is referred to as the unlabeled sample,
   wherein the first calibration section acquires the detected values including the phase information from the respective detection sensors when the unlabeled sample is irradiated as the object to be measured with the laser beam that has been modulated in time at the given frequency, and obtains the fluorescence relaxation time and the gain constant of the autofluorescence that is generated by the unlabeled sample based on the detected values, and
   wherein the matrix producing section produces the correction conversion matrix by using the fluorescence relaxation time and the gain constant obtained by the first calibration section.

8. The fluorescence detecting device according to claim 6,
   wherein the processing section includes a second calibration section that obtains, for each kind of the labeled samples, the fluorescence relaxation time and the gain constant when it is assumed that the fluorescence that is generated by each fluorochrome is a relaxation response of a first order lag system for each kind of the labeled samples,
   wherein the second calibration section acquires the detected values including the phase information from the respective detection sensors when a labeled sample, in which one kind of the fluorochromes is adhered to a sample that generates the autofluorescence is irradiated as the object to be measured with the laser beam that has been modulated in time at the given frequency, obtains the fluorescence relaxation time and a gain constant of the fluorescence that is generated by the fluorochrome of the labeled sample based on the detected values, and obtains fluorescence relaxation times and gain constants of the fluorescence that is generated by all of the fluorochromes included in the labeled samples while changing the kind of the fluorochrome that is adhered to the sample that generates the autofluorescence, and
   wherein the matrix producing section produces the correction conversion matrix by using the fluorescence relaxation times and the gain constants of the labeled samples obtained by the second calibration section.

9. A fluorescence detecting device that irradiates a plurality of labeled samples that are labeled by a plurality of fluorochromes with a laser beam to obtain respective fluorescence intensities based on detected values of fluorescence of the plurality of labeled samples that generate different kinds of fluorescence, comprising:
   a laser light source section that outputs the laser beam with which the object to be measured is irradiated;

a light receiving section that outputs a fluorescence signal of the fluorescence that is generated from the object to be measured which is irradiated with the laser beam;

a light source control section that generates a modulation signal having a given frequency in order to time-modulate an intensity of the laser beam that is output from the laser light source section; and a processing section that calculates a fluorescence relaxation time of the fluorescence of the object to be measured by using the modulation signal based on the fluorescence signal that is output from the light receiving section by irradiating the object to be measured with the time-modulated laser beam, wherein the light receiving section includes a plurality of detection sensors that are different in light receiving wavelength band, for receiving the fluorescence of the labeled samples when the intensity of the laser beam is modulated in time at a given frequency and the labeled samples are irradiated with the laser beam, and wherein the processing section includes:

an input section that acquires, by receiving the fluorescence of the labeled samples by the plurality of detection sensors, the detected values including phase information from the respective detection sensors;

a matrix producing section that sets matrix elements of a correction conversion matrix to produce the correction conversion matrix by using parameters of a transfer function when it is assumed that each fluorescence of the labeled samples that are irradiated with the laser beam is a relaxation response of a first order lag system; and an intensity calculating section that obtains, with a set of the detected values including the phase information acquired from the respective detection sensors as a vector, the fluorescence intensities of the fluorescence that is generated by the respective labeled samples by allowing an inverse matrix produced from the correction conversion matrix to act on the vector.

10. A fluorescence detecting method of obtaining respective fluorescence intensities based on detected values of fluorescence that is generated by irradiating a plurality of labeled samples with a laser beam, the labeled samples being labeled by a plurality of fluorochromes, the fluorescence detecting method comprising the steps of:

time-modulating an intensity of the laser beam in time at a given frequency, irradiating the labeled samples with the time-modulated laser beam, and receiving the fluorescence generated by the labeled samples at this time by a plurality of detection sensors that are different in light receiving wavelength band, to thereby acquire the detected values including phase information from the respective detection sensors;

producing the correction conversion matrix by setting matrix elements of the correction conversion matrix using parameters of a transfer function when it is assumed that each fluorescence of the labeled samples that are irradiated with the laser beam is a relaxation response of a first order lag system; and obtaining, with a set of the detected values including the phase information acquired from the respective detection sensors as a vector, the fluorescence intensities of the fluorescence that is generated by the labeled samples by allowing an inverse matrix produced from the correction conversion matrix to act on the vector.

11. The fluorescence detecting method according to claim 10, wherein the labeled samples includes a plurality different kinds of samples by adhering the fluorochromes that are different in kind from each other to samples that generate autofluorescence with irradiation of the laser beam, and wherein the fluorescence that is generated from at least one kind of fluorochrome among the fluorochromes and the autofluorescence that is generated from the samples have wavelength spectrums partially overlapped each other in a wavelength region by irradiation of the labeled samples with the laser beam.

12. The fluorescence detecting method according to claim 11, wherein when the number of the detection sensors is m and the number of kinds of the fluorochromes is n, $2 \cdot m \geq n+1$ is satisfied.

13. The fluorescence detecting method according to claim 11, wherein the step of producing the correction conversion matrix includes performing a first calibration for obtaining, where a sample to which the fluorochrome is not adhered and which generates the autofluorescence is referred to as an unlabeled sample, a fluorescence relaxation time and a gain constant when it is assumed that the autofluorescence is a relaxation response of a first order lag system for the unlabeled sample, wherein the first calibration includes irradiating the unlabeled sample as an object to be measured with the laser beam that has been modulated in time at the given frequency to acquire the detected values including the phase information from the respective detection sensors, and obtaining a fluorescence relaxation time and a gain constant of the autofluorescence that is generated by the unlabeled sample based on the detected values, and wherein the correction conversion matrix is produced by using the fluorescence relaxation time and the gain constant obtained by the first calibration.

14. The fluorescence detecting method according to claim 13, wherein in the producing of the correction conversion matrix, when the gain constant that is obtained by the first calibration is used in order to produce the correction conversion matrix, gain constants that are obtained from the detected values of the respective detection sensors are used after normalizing the gain constants by a maximum gain constant among the gain constants.

15. The fluorescence detecting method according to claim 13, wherein in the first calibration, the detected values used for obtaining the fluorescence relaxation time and the gain constant comprise amplitude values of a cos component and a sin component of a signal waveform detected by the detection sensors, the detected values including the phase information are acquired for each of the labeled samples, and a representative value is extracted from the plurality of detected values to be used in the first calibration.

16. The fluorescence detecting method according to claim 11, wherein the step of producing the correction conversion matrix includes performing a second calibration for obtaining, for each kind of the labeled samples, the fluorescence relaxation time and the gain constant when it is assumed that the fluorescence that is generated by the fluorochrome is a relaxation response of a first order lag system, for each kind of the labeled samples, wherein the second calibration includes irradiating a labeled sample, in which one kind of the fluorochromes is adhered to a sample that generates the autofluorescence, as the object to be measured with the laser beam that has been modulated in time at the given frequency to acquire the detected values including the phase information from the respective detection sensors, obtaining the fluorescence relaxation time and the gain constant of the fluorescence that is generated by the fluorochrome of the labeled sample based on the detected values, and obtaining fluorescence relaxation times and gain constants of the fluorescence that is generated by all of the fluorochromes included in the labeled samples while changing the kind of the fluorochrome that is adhered to the sample that generates the autofluorescence, and wherein the correction conversion matrix is produced by using the fluorescence relaxation times and the gain constants which are obtained by the second calibration.

17. The fluorescence detecting method according to claim 16, wherein in the obtaining of the fluorescence relaxation times and the gain constants of the fluorescence that is generated by the fluorochromes of the labeled samples, when a sample to which the fluorochrome is not adhered and which generates the autofluorescence referred to as an unlabeled sample, the first calibration for obtaining the fluorescence relaxation time and the gain constant is performed for the unlabeled sample, the fluorescence relaxation time and the gain constant defined when it is assumed that the autofluorescence is a relaxation response of the first order lag system is performed for the unlabeled sample, and wherein the second calibration includes obtaining the fluorescence relaxation times and the gain constants of the fluorescence that is generated by the fluorochromes of the labeled samples by using the fluorescence relaxation time and the gain constant of the fluorescence that is generated by the unlabeled sample, the fluorescence relaxation time and the gain constant of the fluorescence that is generated by the unlabeled sample being obtained based on the detected values including the phase information acquired from the respective detection sensors by irradiating the unlabeled sample as the object to be measured with the laser beam that has been modulated in time at the given frequency in the first calibration.

18. The fluorescence detecting method according to claim 16, wherein in the producing of the correction conversion matrix, when the gain constants obtained by the second calibration are used in order to produce the correction conversion matrix, the gain constants that are obtained from the detected values of the respective detection sensors are normalized by a maximum gain constant among the gain constants of the fluorescence that is generated by the fluorochromes of the respective labeled samples.

19. The fluorescence detecting method according to claim 16, wherein in the second calibration, the deeded values used for obtaining the fluorescence relaxation times and the gain constants comprise amplitude values of a cos component and a sin component of a signal waveform detected by the detection sensors, the detected values including the phase information are acquired for respective labeled samples, and a representative value is extracted from the detected values of the plurality of labeled samples to be used in the second calibration.

* * * * *